(12) United States Patent
Carter et al.

(10) Patent No.: US 7,722,539 B2
(45) Date of Patent: May 25, 2010

(54) TREATMENT OF UNWANTED TISSUE BY THE SELECTIVE DESTRUCTION OF VASCULATURE PROVIDING NUTRIENTS TO THE TISSUE

(75) Inventors: Stephen J. Carter, La Conner, WA (US); Shahram Vaezy, Seattle, WA (US); Roy W. Martin, Anacortes, WA (US); George W. Keilman, Woodinville, WA (US); Lawrence A. Crum, Bellevue, WA (US)

(73) Assignees: University of Washington, Seattle, WA (US); Mirabilis Medica, Seattle, WA (US)

( * ) Notice: Subject to any disclaimer, the term of this patent is extended or adjusted under 35 U.S.C. 154(b) by 1315 days.

(21) Appl. No.: 11/207,554

(22) Filed: Aug. 18, 2005

(65) Prior Publication Data
US 2006/0052701 A1      Mar. 9, 2006

Related U.S. Application Data

(60) Continuation-in-part of application No. 10/770,350, filed on Feb. 2, 2004, which is a continuation-in-part of application No. 10/166,795, filed on Jun. 7, 2002, now Pat. No. 6,716,184, which is a division of application No. 09/397,471, filed on Sep. 17, 1999, now Pat. No. 6,425,867.

(60) Provisional application No. 60/100,812, filed on Sep. 18, 1998.

(51) Int. Cl.
*A61B 8/00*   (2006.01)

(52) U.S. Cl. ............................ 600/439; 601/2; 600/471; 600/462

(58) Field of Classification Search .................. 600/439, 600/471, 462; 601/2
See application file for complete search history.

(56) References Cited

U.S. PATENT DOCUMENTS

RE33,590 E    5/1991   Dory .................... 128/660.03

(Continued)

FOREIGN PATENT DOCUMENTS

| DE | 04230415 A1 | 3/1994 |
| EP | 01265223 B1 | 11/2002 |
| WO | WO 00/72919 | 12/2000 |

OTHER PUBLICATIONS

Yu, T., Wang, G., Hu, K., Ma, P., Bai, J., and Wang, Z. "A microbubble agent improves the therapeutic efficiency of high intensity focused ultrasound: a rabbit kidney study." (Abstract) NDN 234-0481-1539-3. *Urol Res*. Feb. 2004; 32(1): 14-9. Epub Dec. 4, 2003.

(Continued)

*Primary Examiner*—Eric F Winakur
*Assistant Examiner*—Helene Bor
(74) *Attorney, Agent, or Firm*—Ronald M. Anderson

(57) ABSTRACT

A noninvasive technique that can be used to deny blood flow to a particular region of tissue, without the inherent risks associated with invasive procedures such as surgery and minimally-invasive procedures such as embolization. Blood flow in selected portions of the vasculature can be occluded by selectively treating specific portions of the vasculature with high intensity focused ultrasound (HIFU). The occlusion denies undesired tissue the nutrients and oxygen provided by blood flow, causing necrosis in the undesired tissue. An imaging technology (such as magnetic resonance imaging, magnetic resonance angiography, ultrasound imaging, Doppler based ultrasound imaging, or computed tomographic angiography) is used to identify the undesired tissue, and the vascular structures associated with the undesired tissue. A portion of the vasculature providing blood flow to the undesired tissue is selected, and HIFU is administered to the selected portion of the vasculature to occlude blood flow through that portion of the vasculature.

18 Claims, 15 Drawing Sheets

U.S. PATENT DOCUMENTS

| | | | | |
|---|---|---|---|---|
| 5,039,774 | A | 8/1991 | Shikinami et al. | 528/60 |
| 5,065,742 | A | 11/1991 | Belikan et al. | 128/24 |
| 5,080,101 | A | 1/1992 | Dory | 128/660.03 |
| 5,080,102 | A | 1/1992 | Dory | 128/660.03 |
| 5,150,712 | A | 9/1992 | Dory | 128/660.03 |
| 5,219,401 | A | 6/1993 | Cathignol et al. | 128/660.03 |
| 5,311,869 | A | 5/1994 | Okazaki | 128/660.03 |
| 5,391,140 | A | 2/1995 | Schaetzle et al. | 601/4 |
| 5,394,877 | A | 3/1995 | Orr et al. | 600/459 |
| 5,471,988 | A | 12/1995 | Fujio et al. | 128/660.03 |
| 5,474,071 | A | 12/1995 | Chapelon et al. | 60/439 |
| 5,492,126 | A | 2/1996 | Hennige et al. | 600/439 |
| 5,507,790 | A | 4/1996 | Weiss | 607/100 |
| 5,522,878 | A | 6/1996 | Montecalvo et al. | 607/152 |
| 5,526,815 | A | 6/1996 | Granz et al. | 128/660.03 |
| 5,558,092 | A | 9/1996 | Unger et al. | 128/660.03 |
| 5,573,497 | A | 11/1996 | Chapelon | 601/2 |
| 5,666,954 | A | 9/1997 | Chapelon et al. | 600/439 |
| 5,720,286 | A | 2/1998 | Chapelon et al. | 600/439 |
| 5,720,287 | A | 2/1998 | Chapelon et al. | 600/439 |
| 5,762,066 | A * | 6/1998 | Law et al. | 600/439 |
| 5,769,790 | A | 6/1998 | Watkins et al. | 600/439 |
| 5,817,021 | A | 10/1998 | Reichenberger | 600/439 |
| 5,823,962 | A | 10/1998 | Schaetzle et al. | 600/439 |
| 5,827,204 | A | 10/1998 | Grandia et al. | 601/2 |
| 5,833,647 | A | 11/1998 | Edwards | 604/22 |
| 5,873,828 | A | 2/1999 | Fujio et al. | 600/439 |
| 5,895,356 | A | 4/1999 | Andrus et al. | 600/439 |
| 5,906,580 | A * | 5/1999 | Kline-Schoder et al. | 600/459 |
| 5,993,389 | A | 11/1999 | Driscoll, Jr. et al. | 600/371 |
| 6,007,499 | A | 12/1999 | Martin et al. | 601/3 |
| 6,039,694 | A | 3/2000 | Larson et al. | 600/459 |
| 6,050,943 | A | 4/2000 | Slayton et al. | 600/439 |
| 6,071,239 | A | 6/2000 | Cribbs et al. | 600/439 |
| 6,179,831 | B1 | 1/2001 | Bliweis | 606/21 |
| 6,221,015 | B1 | 4/2001 | Yock | 600/439 |
| 6,409,720 | B1 | 6/2002 | Hissong et al. | 606/27 |
| 6,425,867 | B1 | 7/2002 | Vaezy et al. | 600/439 |
| 6,491,672 | B2 | 12/2002 | Slepian et al. | 604/267 |
| 6,595,934 | B1 | 7/2003 | Hissong et al. | 601/3 |
| 6,599,256 | B1 | 7/2003 | Acker et al. | 601/2 |
| 6,626,855 | B1 | 9/2003 | Weng et al. | 601/3 |
| 6,656,136 | B1 | 12/2003 | Weng et al. | 601/2 |
| 6,676,601 | B1 | 1/2004 | Lacoste et al. | 600/439 |
| 6,685,639 | B1 | 2/2004 | Wang et al. | 600/439 |
| 6,716,184 | B2 | 4/2004 | Vaezy et al. | 601/3 |
| 6,719,699 | B2 | 4/2004 | Smith | 600/459 |
| 6,846,291 | B2 | 1/2005 | Smith et al. | 600/459 |
| 2002/0016557 | A1* | 2/2002 | Duarte et al. | 601/2 |
| 2002/0193681 | A1 | 12/2002 | Vitek et al. | 600/411 |
| 2002/0193831 | A1 | 12/2002 | Smith, III | 607/2 |
| 2003/0018255 | A1 | 1/2003 | Martin et al. | 600/437 |
| 2003/0069569 | A1 | 4/2003 | Burdette et al. | 606/27 |
| 2003/0125623 | A1 | 7/2003 | Kelly et al. | 600/437 |
| 2004/0019278 | A1 | 1/2004 | Abend | 600/545 |
| 2004/0030268 | A1 | 2/2004 | Weng et al. | 601/2 |
| 2004/0078034 | A1 | 4/2004 | Acker et al. | 606/27 |
| 2004/0097805 | A1 | 5/2004 | Verard et al. | 600/428 |
| 2004/0097840 | A1 | 5/2004 | Holmer | 601/2 |
| 2004/0143186 | A1 | 7/2004 | Anisimov et al. | 600/437 |
| 2004/0153126 | A1 | 8/2004 | Okai | 607/1 |
| 2004/0181178 | A1 | 9/2004 | Aldrich et al. | 601/3 |
| 2004/0234453 | A1 | 11/2004 | Smith | 424/9.5 |
| 2004/0254620 | A1* | 12/2004 | Lacoste et al. | 607/96 |

OTHER PUBLICATIONS

Ostensen, Jonny, PhD; Bendiksen, Ragner, MSc. "Characterization and Use of Ultrasound Contrast Agents." *Acad Radiol* 2002; 9(suppl 2):S276-S278.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." *Acad Radiol* 2002, 9(suppl 2):S279-S281.

Bauer, A.; Solbiati, L.; Weissman, N. "Ultrasound Imaging with SonoVue: Low Mechanical Index Real-time Imaging." *Acad Radiol* 2002, 9(suppl 2):S282-S284.

Watkin, Kenneth L., PhD; McDonald, Michael A., BS. "Multi-Modal Contrast Agents: A First Step[1]." *Acad Radiol* 2002, 9(suppl 2):S285-S287.

Watkin, Kenneth L., PhD; McDonald, Michael A., BS. "Schematic of the Tube, Cross Section Ultrasound Images of the Tube With Different Contrast Media (CM)." *Acad Radiol* 2002, 9(suppl 2):S288-S289.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non-Gaseous Nanoparticle Contrast Agent[1]," *Acad Radiol* 2002, 9(suppl 2):S290-S293.

Tardy, I.; Pochon, S.; Theraulaz, P. Nanjappan; Schneider, M. "In Vivo Ultrasound Imaging of Thrombi Using a Target-specific Contrast Agent[1]." *Acad Radiol* 2002, 9(suppl 2):S294-S296.

Anand, Ajay et al. "Using the ATL 1000 to collect Domodulated RF Data for Monitoring HIFU Lesion Formation." Center for Industrial and Medical Ultrsound, University of Washington. Abstract. 11pp.

Hatangadi, Ram Bansidhar. "A Novel Dual Axis Multiplanar Transesophageal Ultrasound Probe for Three-Dimensional Echocardiograph." *University of Washington, Department of Sciences and Engineering.* (1994), Abstract. vol. 55-11B: .

"Mechanical Bioeffects in the prescence of gas/carrier ultrasound contrast agents." J Ultrasound Med. 19: 120/142, 2000.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305/1320, 1999. Copyright 1999 World Federation for Ultrasound in Medicine & Biology.

Chen, Wen/Shiang, et al. "A comparison of the fragmentation thresholds and inertial cavitation doses of different ultrasound contrast agents." J. Acoust. Soc. Am. 113 (1), Jan. 2003: pp. 643/651.

Chen, Wen/Shiang, et al. "Inertial Cavitation Dose and Hemolysis Produced in Vitro with or Without Optison." Ultrasound in me. & Biol., vol. 29, No. 5, pp. 725/737, 2003.

Dayton, Paul, A., et al. "The magnitude of radiation force on ultrasound contrast agents." J. Acoust. Soc. Am. 112 (5) Pt. 1, Nov. 2002: pp. 2183/2192.

Everbach, Carr, E. and Charles W. Francis. "Cavitational Mechanisms in Ultrasound/Accelerated Thrombolysis at 1 MHz." Ultrasound in Med. & Biol., vol. 26, No. 7, pp. 1153/1160, 2000. Copyright 2000 World Federation in Medicine and Biology.

Guzman, Hector R., et al. "Ultrasound—Mediated Disruption of Cell Membranes. I. Quantification of Molecular uptake and Cell Viability." J. Acoust. Soc. Am. 110 (1), Jul. 2001: pp. 588/595.

Guzman, Hector R., et al. "Ultrasound/mediated disruption of cell membranes. II. Heterogeneous effects on cells." J. Acoust. Soc. Am 110 (1), Jul. 2001: pp. 597/606.

Holt, Glynn, R., Roy, Ronald, A., Edson, Patrick A., Yang, Xinmai. "Bubbles and Hifu: the Good, the Bad and the Ugly." *Boston University, Department of Aerospace and Mechanical Engineering*, Boston, MA 02215: 120/131.

Hynynen, Kullervo, et al. "Potential Adverse Effects of High/Intensity Focused Ultrasound Exposure on Blood Vessels in Vivo." Ultrasound in Med. & Biol., vol. 22, No. 2, pp. 193/201, 1996.

Indman, Paul, MD,. "Alternatives in Gynecology." Hysteroscopy© 2000 OBGYN.net <http://www.gynalternatives.com/hsc.html>.

Ka/yun Ng, Yang Liu. "Therapeutic Ultrasound: Its Application in Drug Delivery." Medicinal Research Reviews, vol. 22, 204/223, 2002 © 2002 John Wiley & Sons, Inc.

Kaczkowski, Peter J., Vaezy, Shahram, Martin, Roy, Crum, Lawrence. "Development of a High Intensity Focused Ultrasound System for image/guided ultrasonic surgery." Ultrasound for Surgery 2001. <http://cimu.apl.washington.edu/hifusurgerysystem.html>.

Miller, Morton W. et al. "A Review of In Vitro Bioeffects of Intertial Ultrasonic Cavitation From a mechanistic Perspective." Ultrasound in Med & Biol., vol. 22, No. 9, pp. 1131/1154, 1996.

Nobuki Kudo, Takehiro Miyaoka, Kengo Okada, and Katsuyuki Yamamoto. "Study on Mechanism of Cell Damage Caused by Microbubbles Exposed to Ultrasound." *Graduate School of Engineering, Hokkaido University, Japan, Research Institute for Electronic Science, Hokkaido University*, 060/0812 Japan.

Owaki, T., Nakano, S. Arimura, K., Aikou, T. "The Ultrasonic Coagulating and Cutting System Injuries Nerve Function." *First Department of Surgery, Kagoshima University School of Medicine, Kagoshima, Japan, Endoscopy*. (2002) 575/579.

Physicians. "Breast Cancer—Insightec: focused ultrasound for non invasive treatment." FAQ <http://www.exablate2000.com/physicians_faq.html>.

Poliachik, Sandra L., et al. "Activation, Aggregation and Adhesion of Platelets Exposed to High/Intensity Focused Ultrasound." Ultrasound in Med. & Biol., vol. 27, No. 11, pp. 1567/1576, 2001.

Poliachik, Sandra L., et al. "Effect of High—Intensity Focused Ultrasound on Whole Blood with or without Microbubble Contrast Agent." Ultrasound in Med. & Biol., vol. 25, No. 6, 1999: 991/998.

Porter, T.R., Xie, F. "Ultrasound, Microbubbles and Thrombolysis." Progress in Cardiovascular Diseases, vol. 44, No. 2, Oct. 2001: 101/110.

Rivens, I.H., Rowland, I.J., Denbow, M., Fisk, N.M., Harr, G.R., Leach, M.O. "Vascular occlusion using focused ultrasound surgery for use in fetal medicine." *European Journal of Ultrasound* 9 (1999): 89/97.

Rosenschein, Uri, et al. "Ultrasound Imaging/Guided Nonivasive Ultrasound Thrombolysis/Preclinical Results." © 2000 American Heart Association, Inc. (Circulation. 2000;102:238/245.) <http://www.circulationaha.com.org>.

Rosenschein, Uri, et al. "Shock/Wave Thrombus Ablation, A New Method for Noninvasive Mechanical Thrombolysis." The American Journal of Cardiology, vol. 70, Issue 15, Nov. 1992: pp. 1358/1361.

Tachibana, Katsuro and Shunro MD., PhD. "The Use of Ultrasound for Drug Delivery." *First Department of Anatomy, Fukuoka University School of Medicine*, Nanakuma, Japan,Echocardiography. (2001) 323/328.

Tachibana, Katsuro, and Shunro M.D., Ph.D. "Albumin Microbubble Echo/Contrast Material as an Enhancer for Ultrasound Accelerated Thrombolysis." (Circulation, 1995; 92: 1148/1150.) © 1995 American Heart Association, Inc.

Vaezy, Shahram et al. 2001. "Acoustic surgery." *Physics World* (August): 35/39.

Vaezy, Shahram et al. 2001. "Experimental Investigations and Device Development." First International Workshop on the Application of HIFU in Medicine. (May 10/13): 4pp.

* cited by examiner

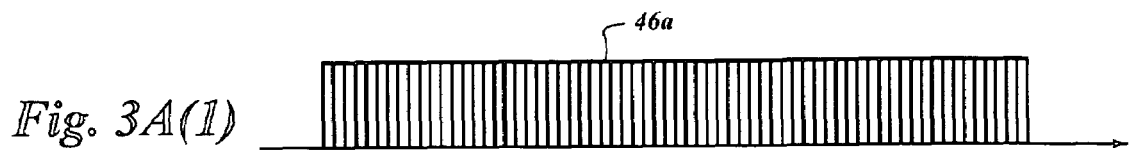
*Fig. 3A(1)*
*Fig. 3A(2)*
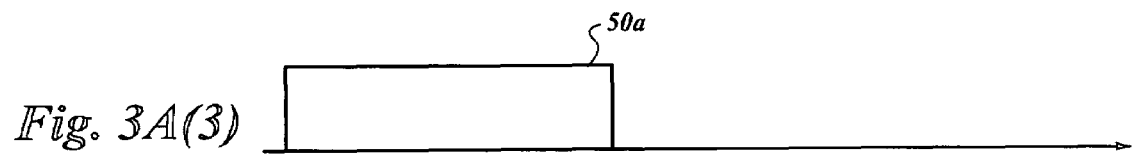
*Fig. 3A(3)*
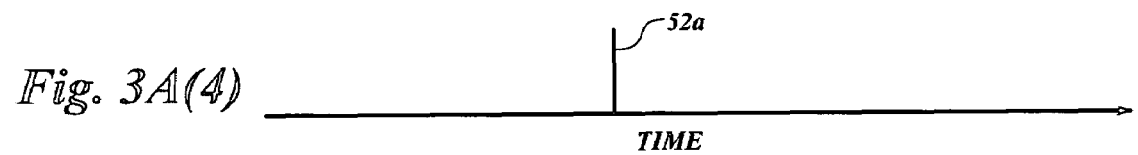
*Fig. 3A(4)*
TIME
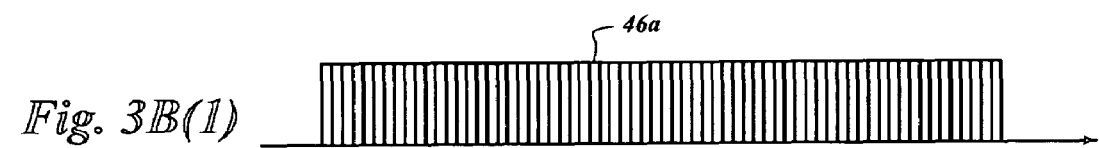
*Fig. 3B(1)*
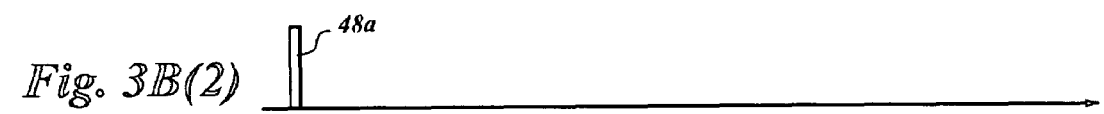
*Fig. 3B(2)*
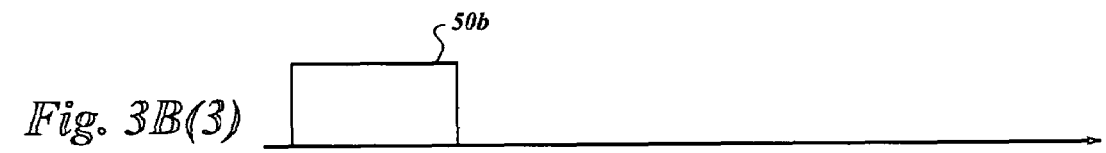
*Fig. 3B(3)*
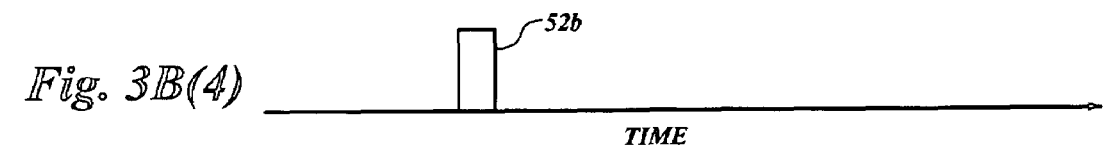
*Fig. 3B(4)*
TIME

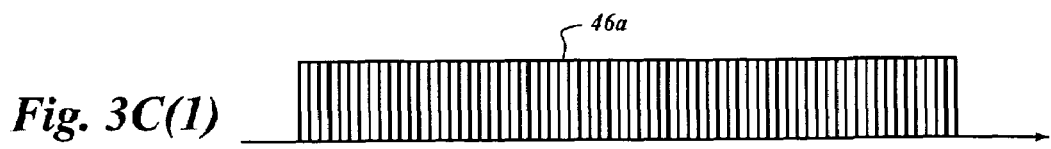
*Fig. 3C(1)*
*Fig. 3C(2)*
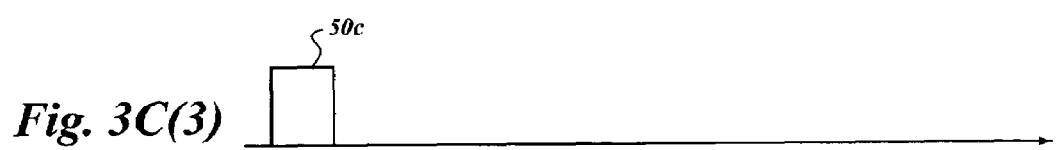
*Fig. 3C(3)*
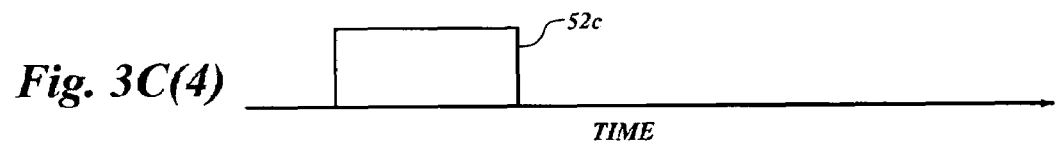
*Fig. 3C(4)*
TIME
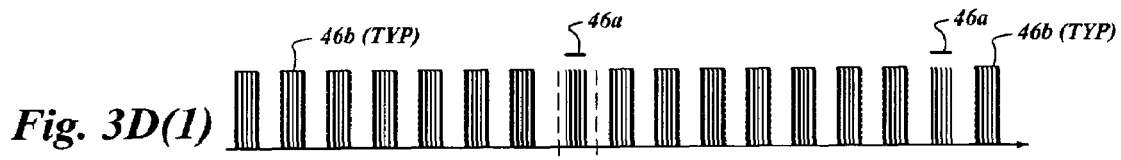
*Fig. 3D(1)*
*Fig. 3D(2)*
*Fig. 3D(3)*
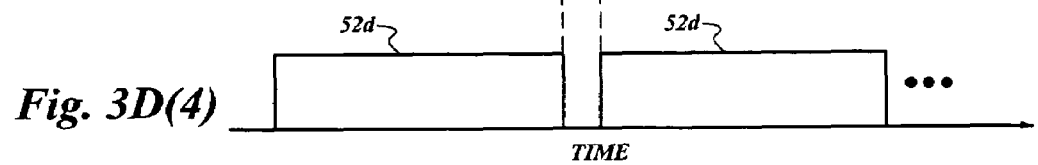
*Fig. 3D(4)*
TIME

TREATMENT OF UNWANTED TISSUE BY THE SELECTIVE DESTRUCTION OF VASCULATURE PROVIDING NUTRIENTS TO THE TISSUE

RELATED APPLICATIONS

This application is a continuation-in-part application of prior copending application Ser. No. 10/770,350, filed on Feb. 2, 2004, which itself is a continuation-in-part application of prior copending application Ser. No. 10/166,795, filed on Jun. 7, 2002 and now issued as U.S. Pat. No. 6,716,184, which itself is a divisional application of prior copending application Ser. No. 09/397,471, filed on Sep. 17, 1999 and now issued as U.S. Pat. No. 6,425,867, which is based on a prior provisional application Ser. No. 60/100,812, filed on Sep. 18, 1998, the benefits of the filing dates of which are hereby claimed under 35 U.S.C. §119(e) and 35 U.S.C. §120.

GOVERNMENT RIGHTS

This invention was made with U.S. Government support under grant No. N00014-01-96-0630 awarded by the Department of the Navy. The U.S. Government has certain rights in the invention.

BACKGROUND

High-intensity focused ultrasound (HIFU) has emerged as a precise, non-surgical, minimally-invasive treatment for benign and malignant tumors. At focal intensities (1,000-10,000 W/cm$^2$) that are 4-5 orders of magnitude greater than that of diagnostic ultrasound (approximately 0.1 W/cm$^2$), HIFU can be applied transcutaneously to induce lesions (i.e., localized tissue necrosis) at a small, well defined region (approximately 1 mm) deep within tissue, while leaving intervening tissue between the HIFU transducer and the focal point essentially unharmed. Tissue necrosis is a result of tissue at the focal point of the HIFU beam being heated to over 70° C. in a very short period of time (generally less than one second). Tissue necrosis also results from cavitation activity, which causes tissue and cellular disorganization. HIFU is currently being used clinically for the treatment of prostate cancer and benign prostatic hyperplasia, as well as the treatment of malignant bone tumors and soft tissue sarcomas. Clinical trials are currently being conducted for HIFU treatment of breast fibroadenomas, and various stage-4 primary and metastatic cancerous tumors of the kidney and liver.

Therapeutic uses of HIFU have generally been directed at destroying undesired masses of tissue by directly targeting the tissue itself. However, the focal region of a HIFU transducer is relatively small (approximately the size of a grain of rice). Thus, to treat the entire volume of even a relatively small tumor with HIFU to necrose the tumorous tissue requires constantly changing the position of the focal region of the HIFU transducer relative to the tumor, leading to relatively long treatment times, and requiring relatively complicated targeting systems. It would be desirable to provide a technique for utilizing HIFU's ability to non-invasively destroy undesired tissue, such as a tumor, without requiring treatment of the entire volume of the undesired tissue.

SUMMARY

The present disclosure relates to the destruction of undesired tissue by selectively targeting vasculature providing nutrients to the undesired tissue. Embolization is an invasive surgical process in which a blood vessel or organ is occluded by physical or chemical means. Generally, a catheter is introduced into a blood vessel, and objects, such as polyvinyl alcohol beads, are introduced into the blood vessel to occlude blood flow from that blood vessel. Embolization is performed to stop bleeding of punctured blood vessels, or to deny blood flow to a particular region of tissue, such as a tumor. The present disclosure is directed to a noninvasive technique that can be used to deny blood flow to a particular region of tissue, without the inherent risks associated with invasive procedures such as embolization. According to the techniques described herein, blood flow in selected portions of the vasculature can be occluded by selectively treating specific portions of the vascular system with HIFU. By denying undesired tissue the nutrients and oxygen provided by blood flow, the techniques described below will cause necrosis in the undesired tissue, thereby reducing the volume of such undesired tissue, or eliminating the undesired tissue.

Initially, some type of imaging technology will be used to identify the undesired tissue, and the vascular structures associated with the undesired tissue. A portion of the vasculature providing blood flow to the undesired tissue will be selected, such that when blood flow through that portion of the vasculature is occluded, blood flow to the undesired tissue will be reduced or eliminated. HIFU is used to target the selected portion of the vasculature to occlude blood flow through that portion of the vasculature. Imaging technologies can then be used to determine whether blood flow to the undesired tissue has been reduced to a desired degree. If further reduction of blood flow to the undesired tissue is desired, additional vascular structures can be targeted. Several different imaging technologies can be used, including but not limited to magnetic resonance imaging, magnetic resonance angiography, ultrasound imaging, Doppler based ultrasound imaging, advanced ultrasound imaging modalities (such as harmonic imaging, pulse inversion, and contrast enhanced B-mode) and computed tomographic angiography.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 1A-1C respectively illustrate ultrasonic images generated during the simultaneous use of ultrasound for imaging and therapy according to the prior art, the pulsing of the HIFU in a conventional scanned image, and the synchronized pulsing of the HIFU and the scan image so as to shift the noise away from a displayed treatment site;

FIG. 2 is a block diagram illustrating the components of a system capable of simultaneously using ultrasound for imaging and therapy;

FIGS. 3A(1)-3D(4) illustrate timing and synchronization patterns that enable the simultaneous use of ultrasound for imaging and therapy;

FIG. 4 illustrates yet another timing and synchronization pattern for synchronizing the HIFU and imaging scans;

FIGS. 5A and 5B respectively illustrate a schematic view of individual external imaging and therapeutic ultrasonic transducers being used for the simultaneous imaging and treatment of a tumor in a female reproductive system, and an ultrasonic image that would thus be generated;

Figure 5A:
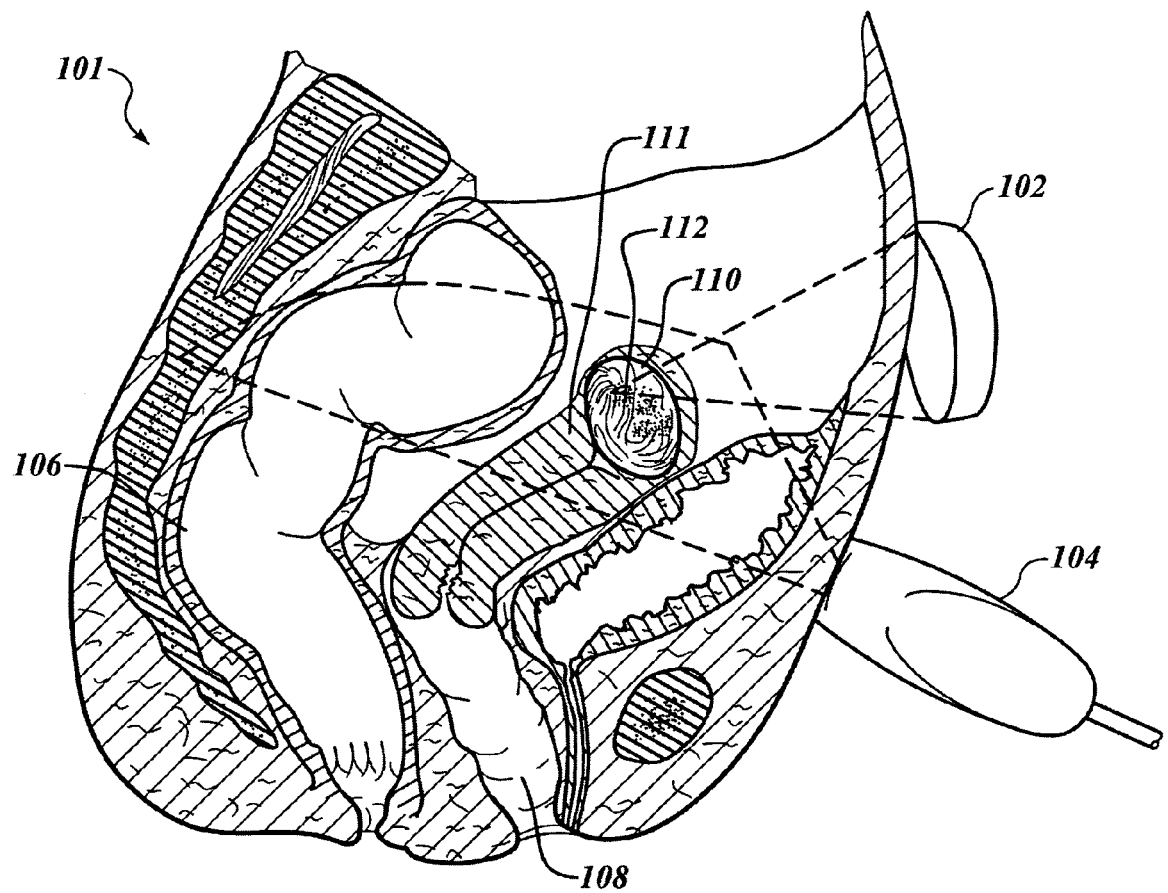
Figure 5B:
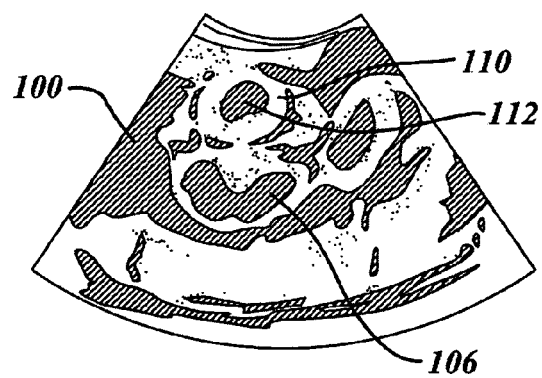
Figure 8A:
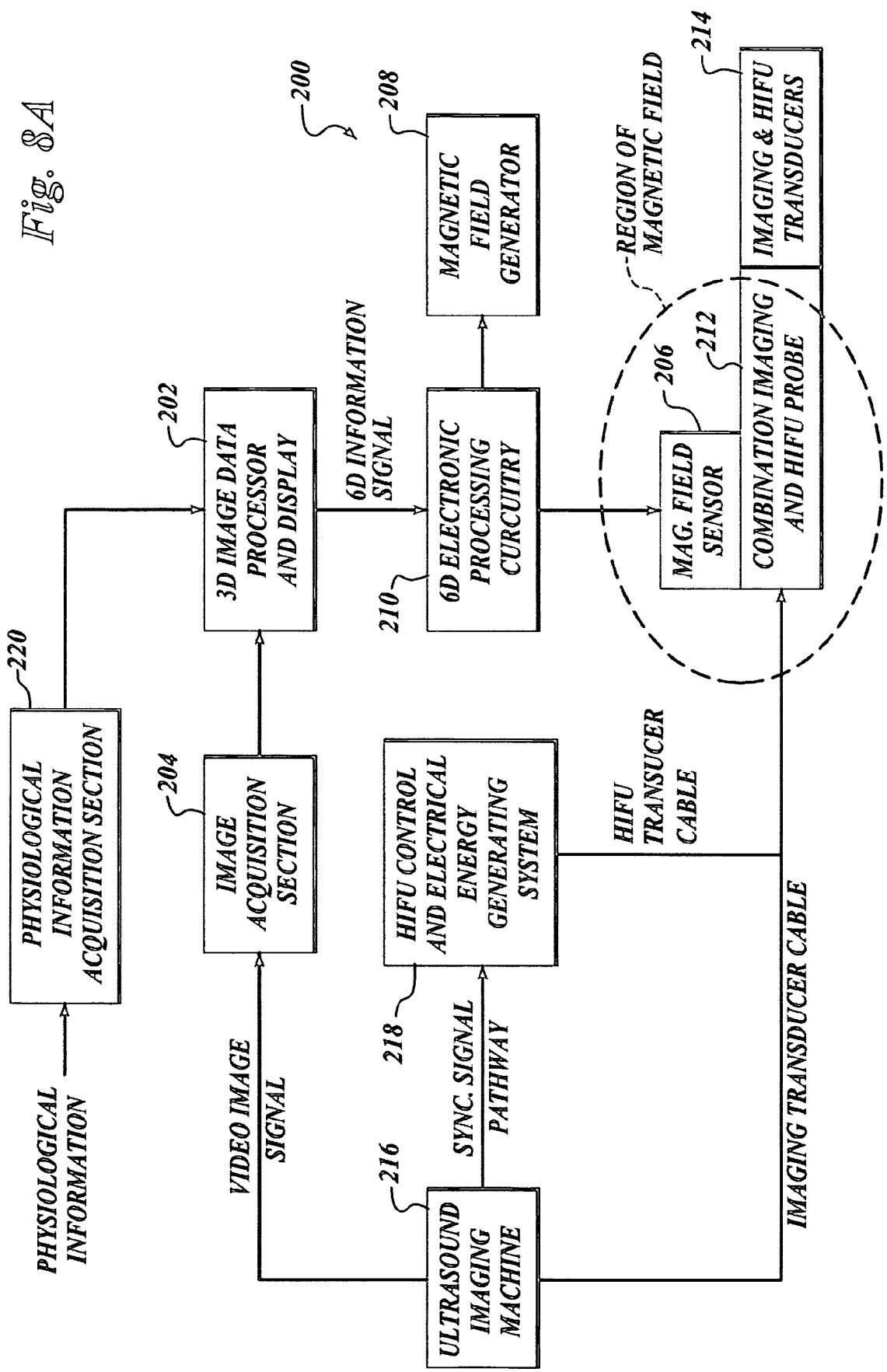
FIG. 8A is a schematic block diagram of a 3D imaging and HIFU therapy system that enables the HIFU therapy to be applied at selected treatment sites in a 3D image of a target area.
Figure 8B:
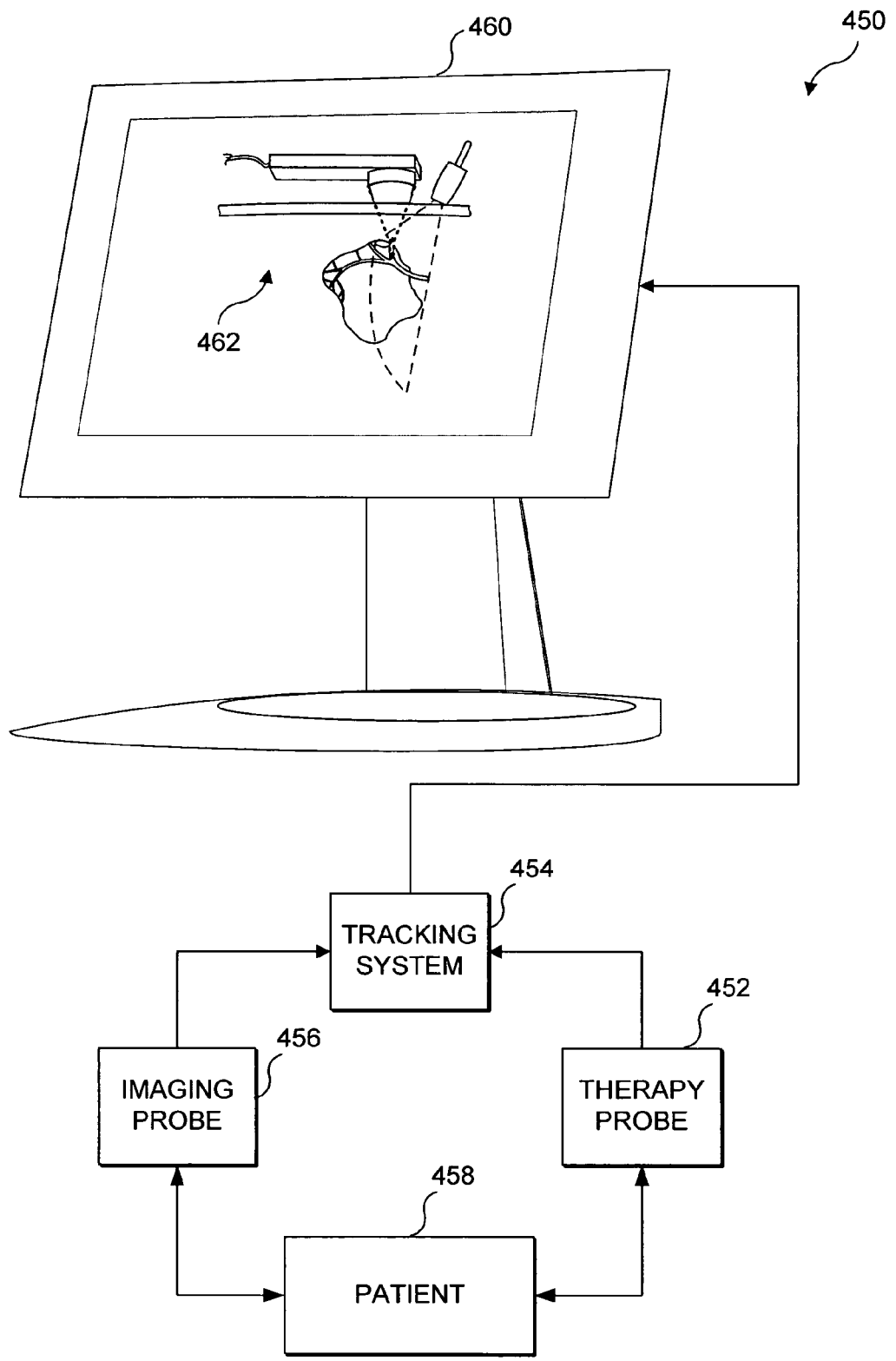
FIG. 8B is a block diagram schematically illustrating the elements of a system to facilitate free hand visualization of the focal point of a HIFU beam during therapy.
Figure 8C:
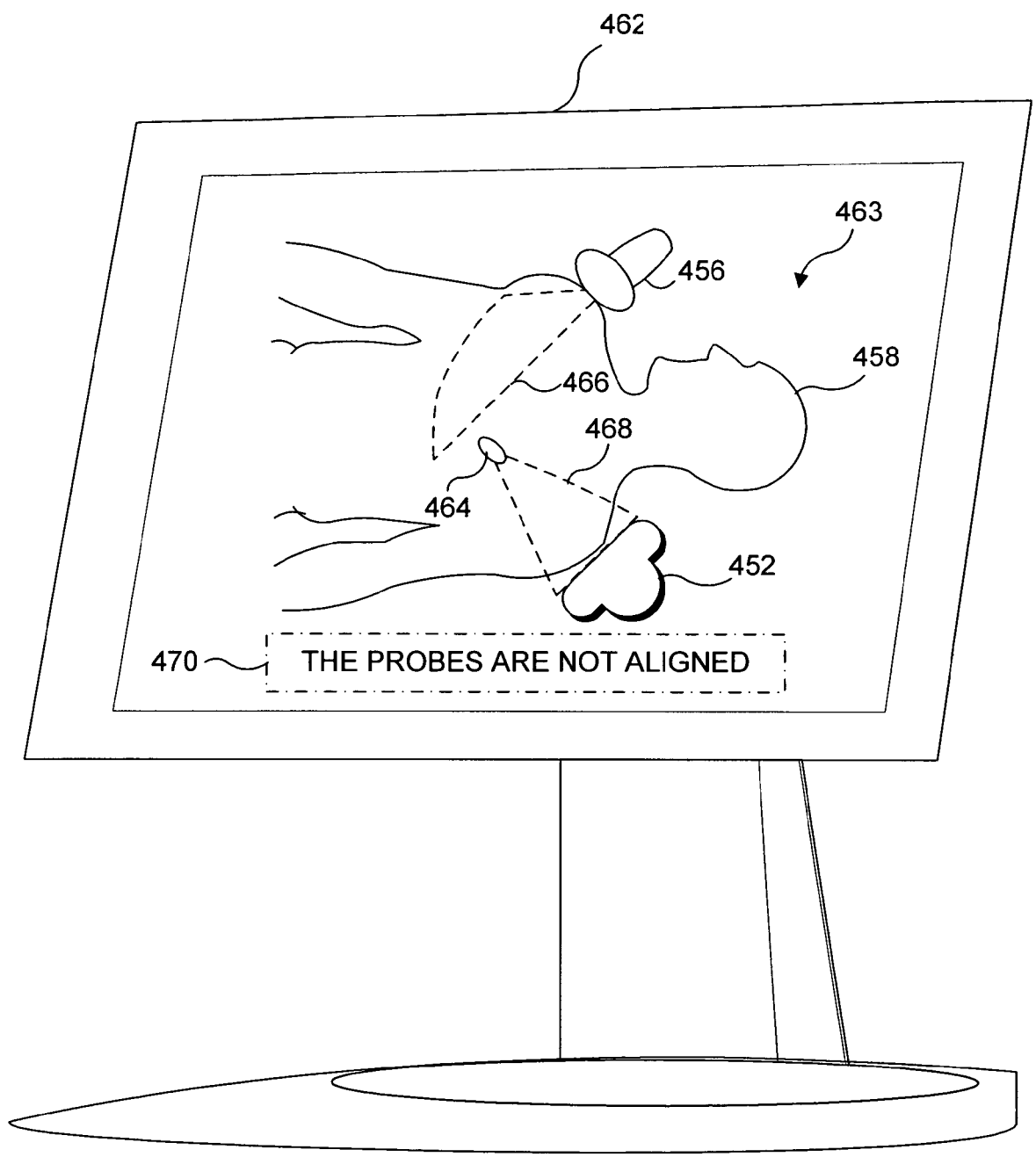
Figure 9:
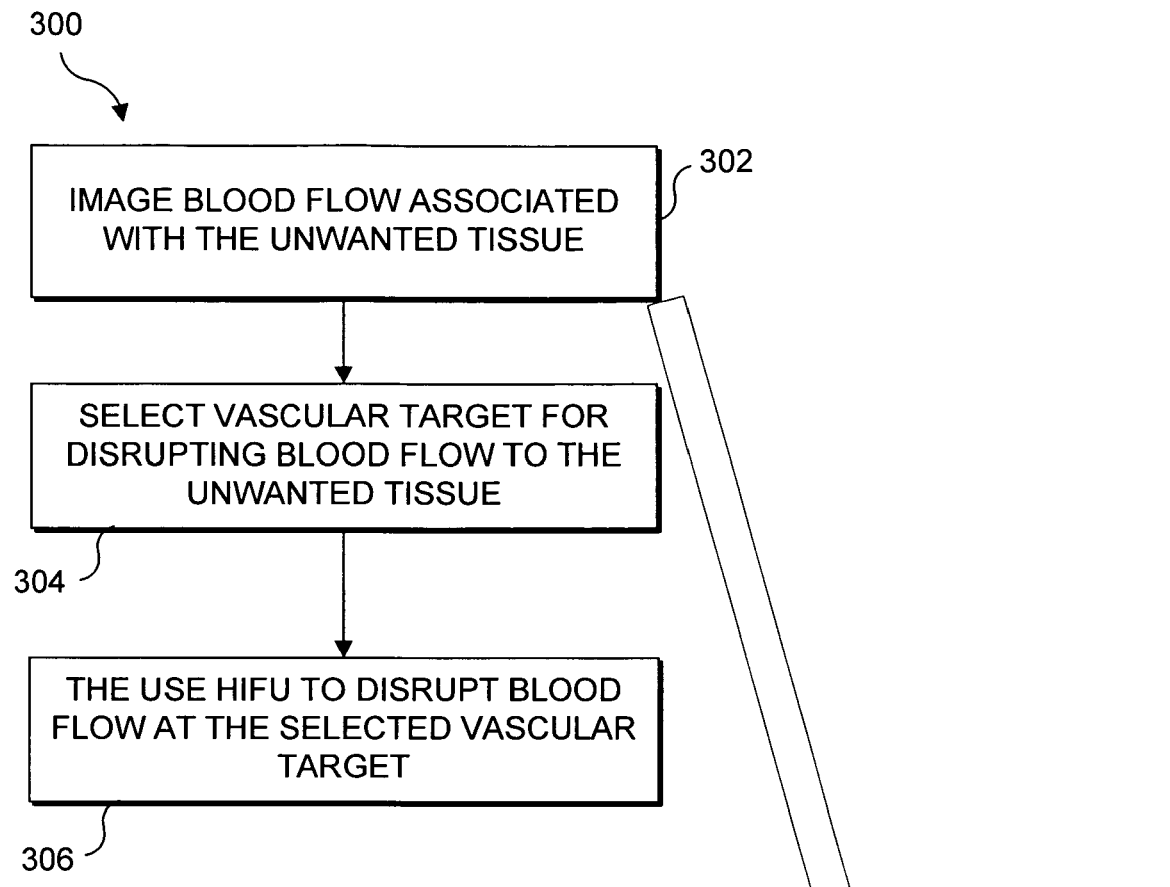
Figure 10A:
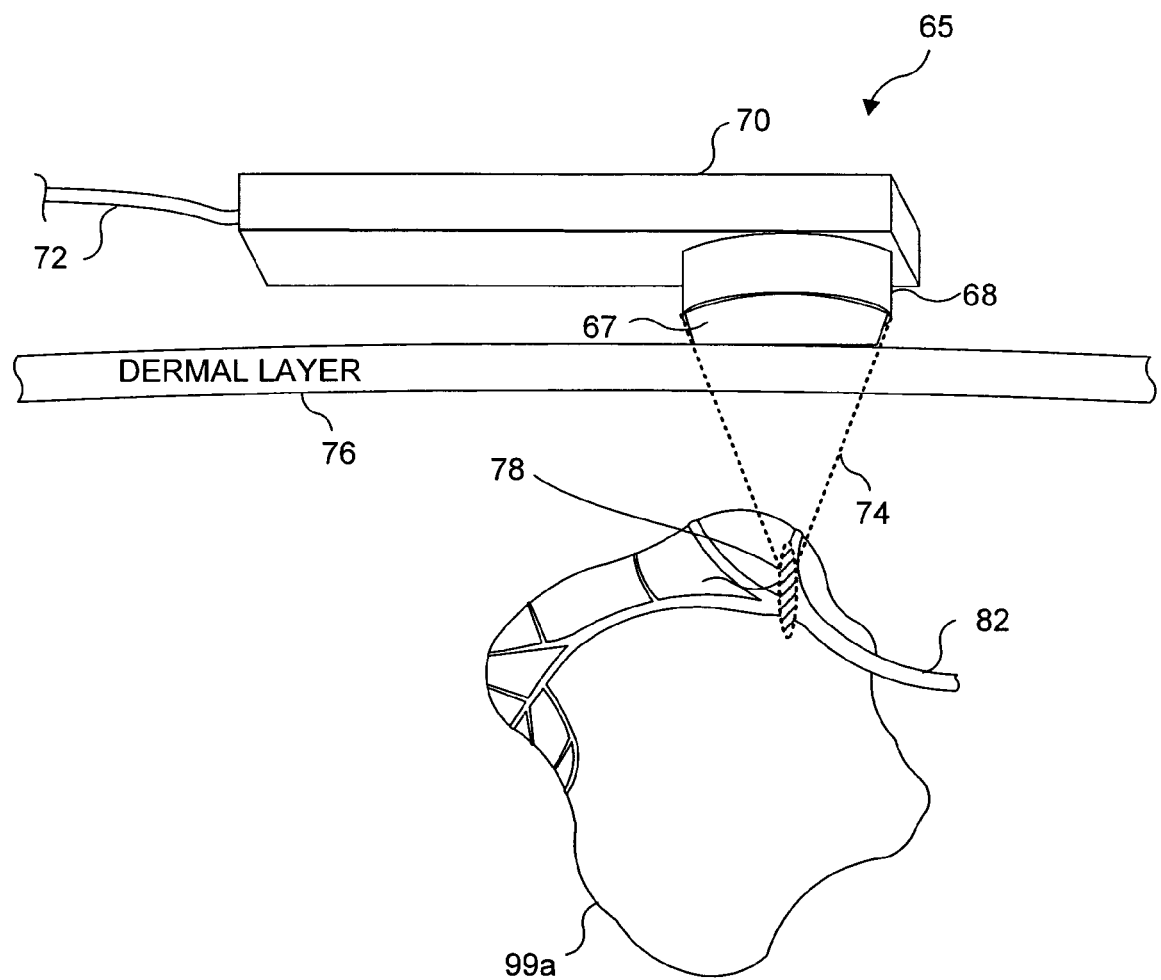
Figure 10B:
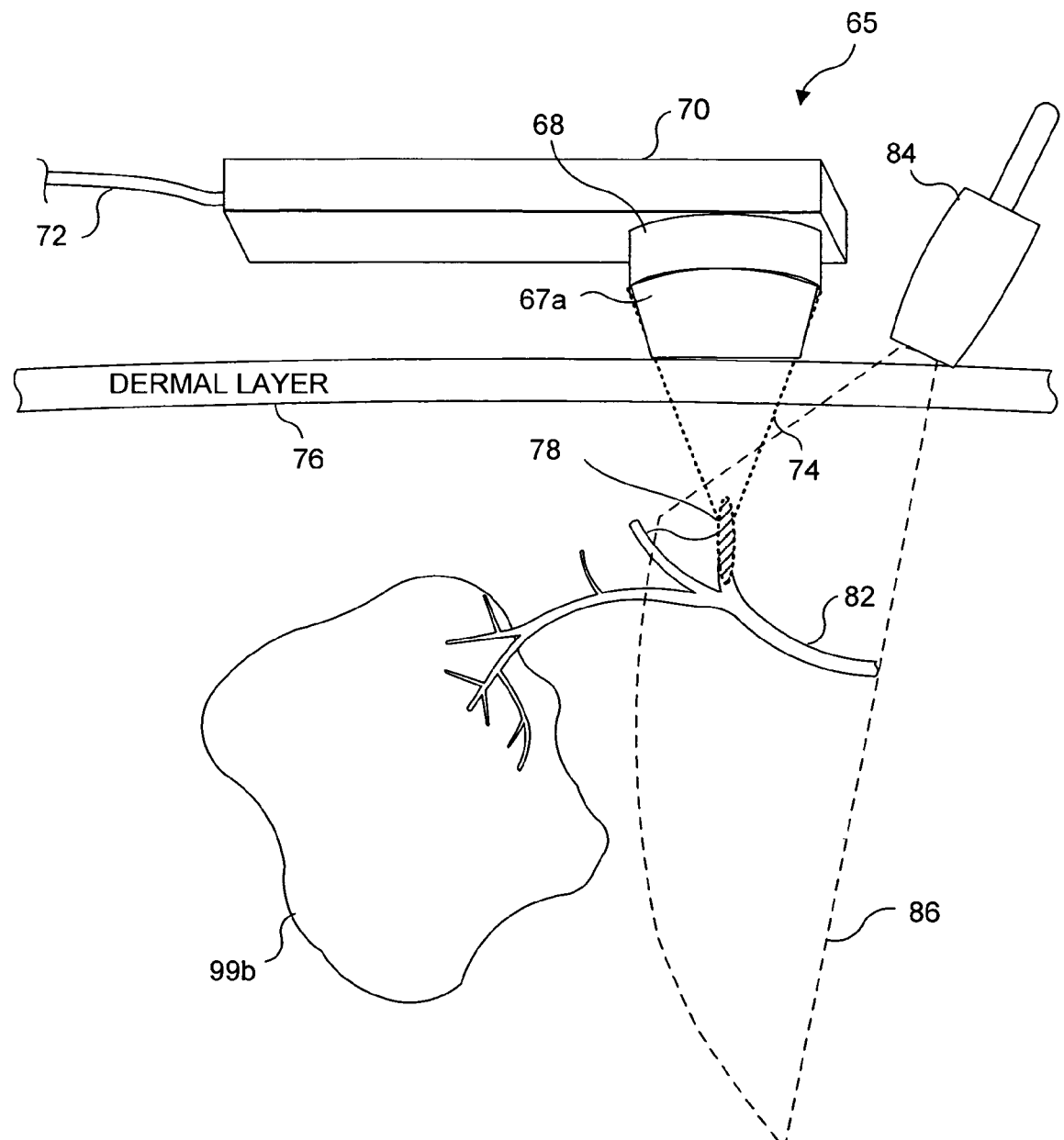
Figure 10C:
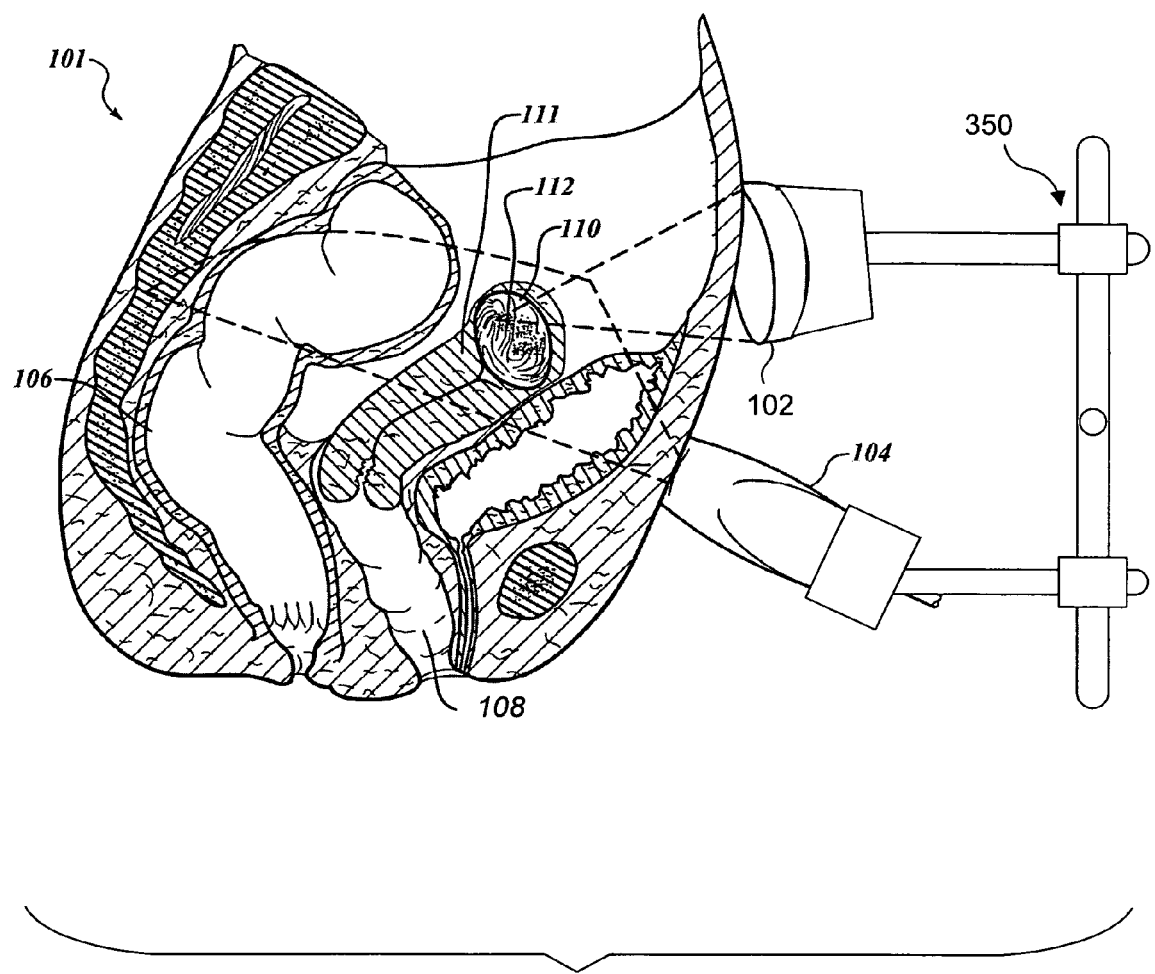
Figure 11:
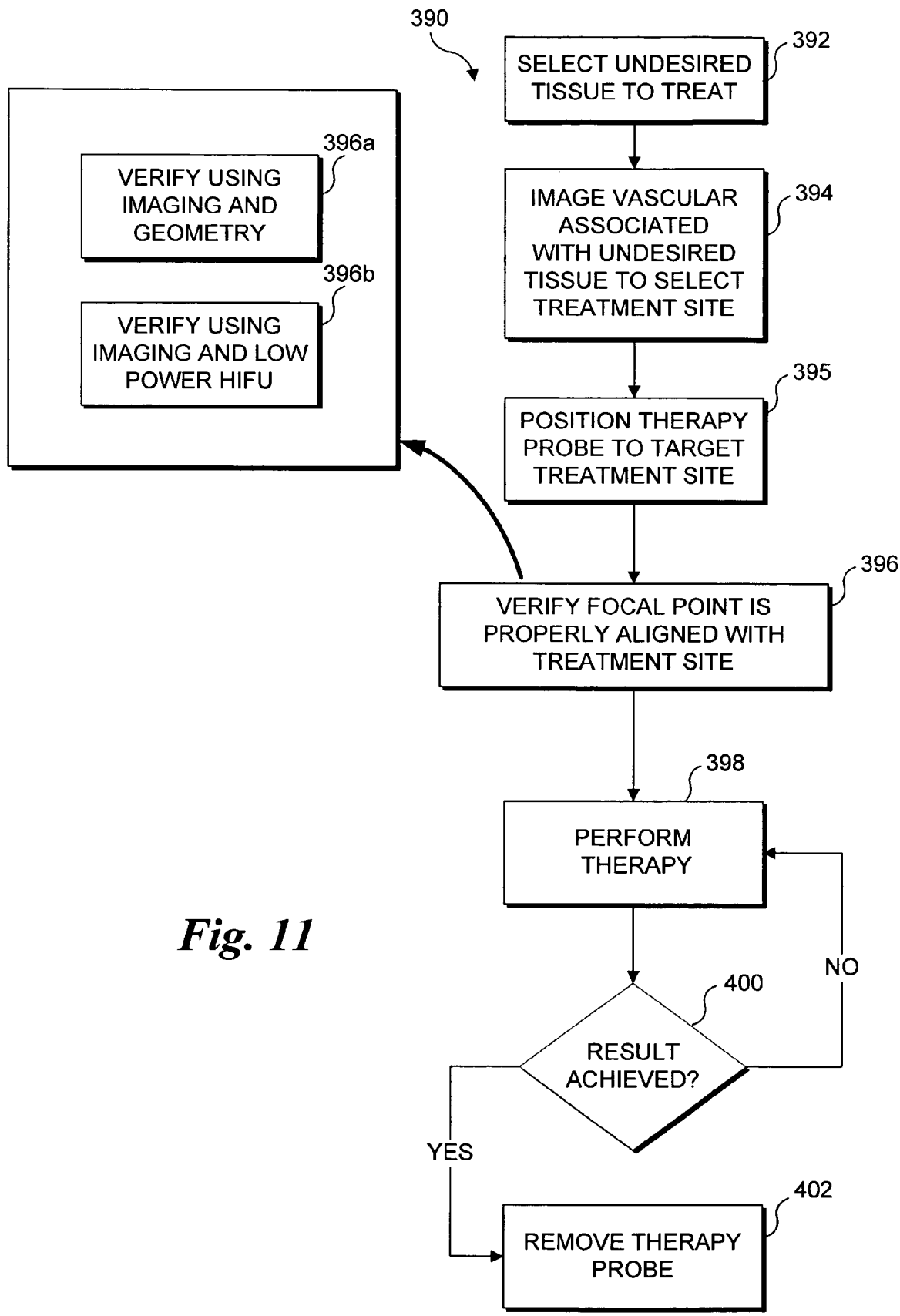
Figure 12:
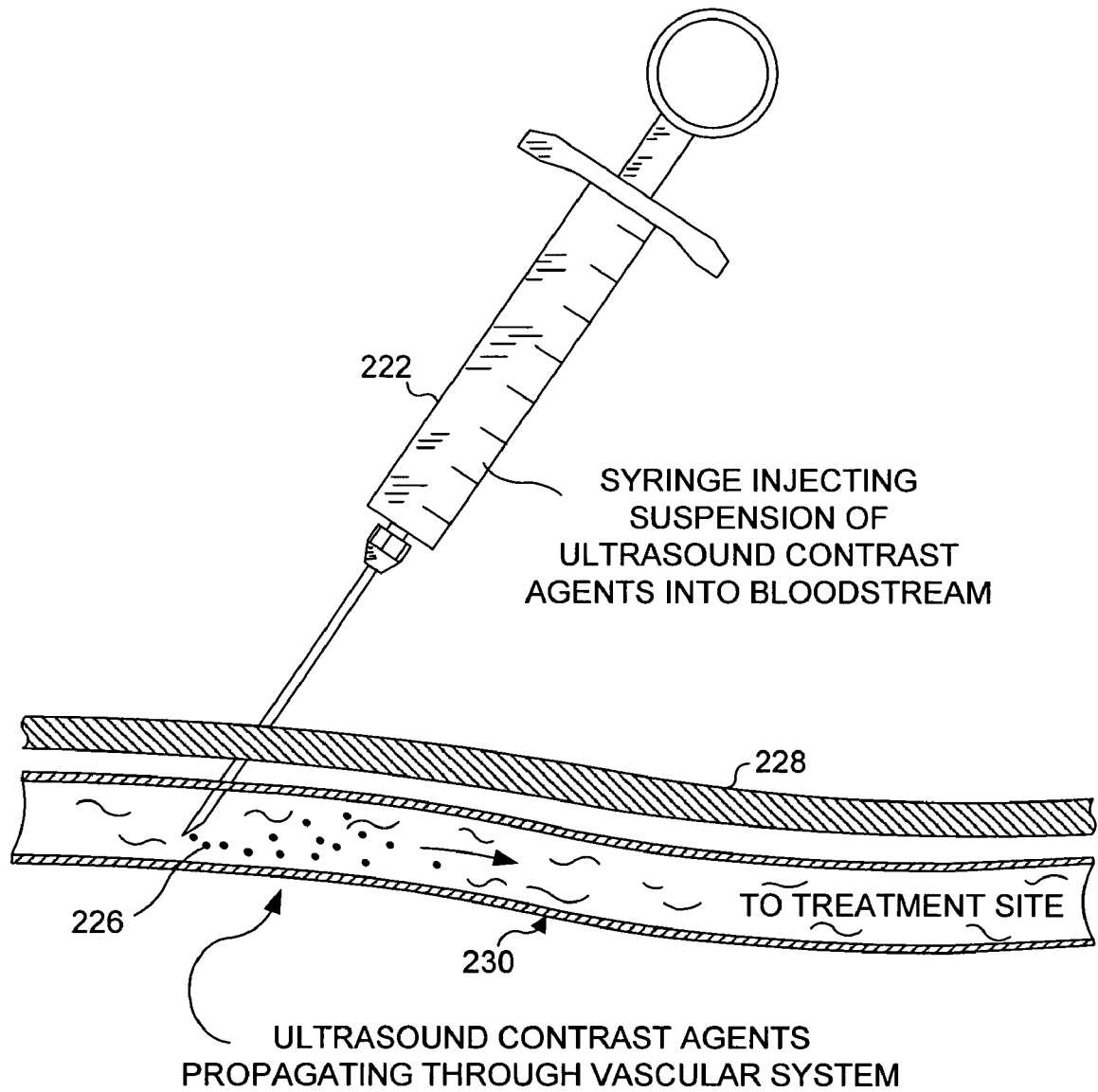

FIG. 8C schematically illustrates an exemplary image provided by the system of FIG. 5B, enabling a clinician to determine how to manipulate a spatial relationship between an imaging probe and a therapy probe to ensure visualization of the focal point of a HIFU beam during therapy;

FIG. 9 is a flowchart illustrating the logical steps implemented in a method for using HIFU therapy to the vascular system in order to treat undesired tissue;

FIG. 10A schematically illustrates a HIFU therapy probe being employed to deliver HIFU transcutaneously to a sub dermal vascular target;

FIG. 10B schematically illustrates an imaging probe and a HIFU therapy probe being used together to achieve transcutaneous image guided HIFU therapy of a vascular target;

FIG. 10C schematically illustrates a frame configured to maintain a spatial orientation between an imaging probe and a therapy probe during administration of HIFU therapy;

FIG. 11 is a flowchart illustrating in greater detail, exemplary logical steps implemented in a method for applying HIFU therapy to the vascular system in order to destroy undesired tissue; and FIG. 12 schematically illustrates an exemplary approach for introducing ultrasound contrast agents into a patient's vascular system in order to facilitate visualization of vascular structures associated with undesired tissue.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive.

Several related concepts are disclosed herein. Portions of the following disclosure are directed to exemplary techniques for simultaneously employing therapeutic HIFU and real time ultrasound imaging. Still other portions of the following disclosure are directed to exemplary techniques for destroying undesired tissue, such as a tumor, by targeting the vascular structures providing nutrients to the undesired tissue. By cutting off the nutrient supply to the undesired tissue, the undesired tissue will necrose, without requiring treatment of the entire mass of the undesired tissue.

Synchronizing Imaging and HIFU to Achieve Real-Time Image Guided Therapy

When administering HIFU therapy, it is very desirable to be able to observe a treatment site, to ensure that lesions induced by the HIFU therapy are being produced at the desired location. Failure to properly aim the HIFU beam will result in undesired tissue necrosis of non-target tissue. From a practical standpoint, this goal has not proven easy to accomplish when ultrasound is used to visualize the focal point, because the HIFU beam used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is out, the light from the stars is completely overwhelmed by the light from the sun, and a person looking into the sky is unable to see any stars, because the bright light from the sun makes the dim light coming from the stars substantially imperceptible. Similarly, the HIFU emitted by the therapy transducer completely overwhelms the ultrasonic waves produced by the imaging transducer, and any ultrasonic image generated is completely saturated with noise caused by the HIFU emitted from the therapeutic transducer.

Figure 1A:
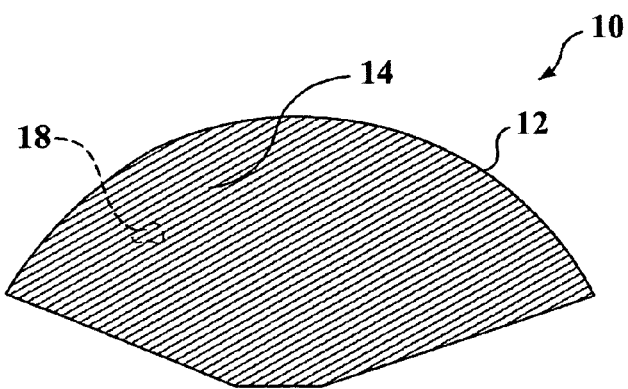

FIG. 1A illustrates an ultrasound image 10 in which a scanned image field 12 is completely obscured by noise 14, as is typical during the simultaneous reception of energy from a reflected imaging pulse and a HIFU wave (neither shown). In regard to ultrasound image 10, a clinician may desire to focus the HIFU wave on a treatment site 18. However, because noise 14 completely saturates scanned image field 12, it is virtually impossible to accurately focus the HIFU wave onto treatment site 18. If the therapy transducer is completely de-energized, noise 14 is eliminated from the scanned image field. However, although the image can then be produced in response to the reflected imaging pulse, the focal point of the HIFU wave will not be seen, and thus, the HIFU wave cannot be accurately focused on treatment site 18. While some change in echogenicity at the HIFU focal point will persist for a time after the HIFU wave is no longer present, any change in a position of the therapy transducer (or treatment site 18) will not register until the therapeutic transducer is re-energized. Thus, the HIFU wave cannot be focused in real-time.

Some prior art systems have included a targeting icon in an ultrasound image to indicate the position of the known focal point of a specific HIFU transducer in a scanned image. While this icon may be helpful in determining whether the HIFU was previously focused, it still does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer.

Figure 1B:
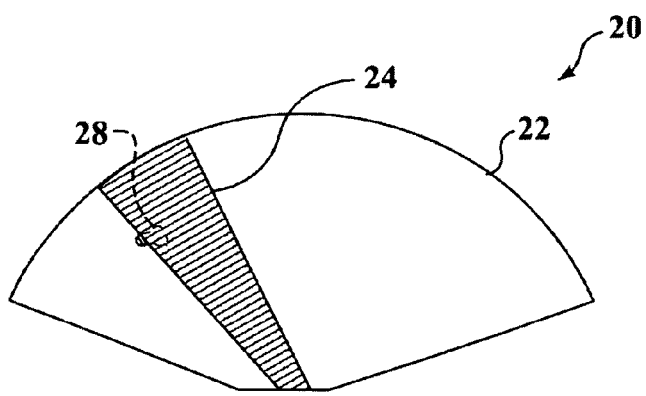

FIG. 1B illustrates one technique in which the effect of noise disrupting the ultrasound image is reduced. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging pulses generated by the scanning transducer. In FIG. 1B, noise 24 substantially masks a treatment site 28. This result will not occur in all cases, because to an observer, noise 24 will move across scanned field 22 as the interference between the HIFU waves and the imaging pulses varies in time. Pulsing of the HIFU wave alone can thus enable the clinician to view a noise-free image of the treatment site only when noise 24 is randomly shifted to a different part of scanned field 22, away from the treatment site. However, this pulsing of the HIFU beam generates an image that is extremely distracting to a clinician, as noise 24 flickers across scanned field 22, making it difficult to concentrate and difficult to consistently determine where the focal point of the HIFU wave is relative to the treatment site, in real-time.

Figure 1C:
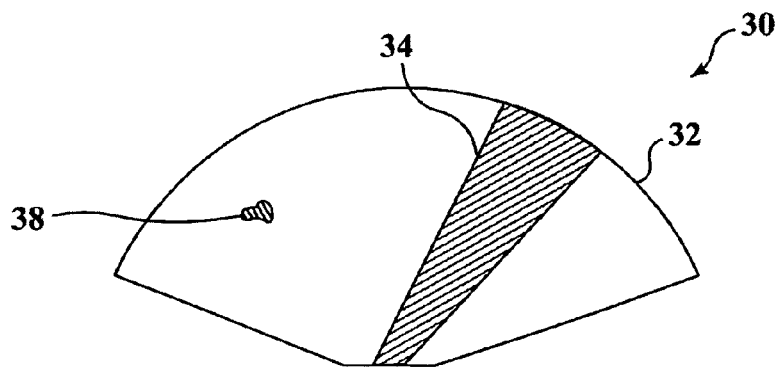

FIG. 1C illustrates an ultrasound image 30 in which a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 of the image that is spaced apart from treatment site 38, by selectively adjusting both the pulsing and the synchronization of the HIFU wave relative to the image pulses. Preferably, noise 34 is shifted completely away from treatment site 38, enabling the clinician to view a noise-free, stable image of treatment site 38 that clearly shows the location of the focal point of the HIFU wave relative to the treatment site. Thus, the HIFU wave can be focused in real-time onto treatment site 38, and a clinician can, in real-time, view the therapeutic effects of the HIFU wave on treatment site 38. It will therefore be apparent that a clinician can de-energize the therapeutic transducer, terminating the generation of the HIFU wave as soon as a desired therapeutic effect has been achieved at the treatment site. In this manner, undesired effects on non-target tissue can be minimized.

Figure 2:
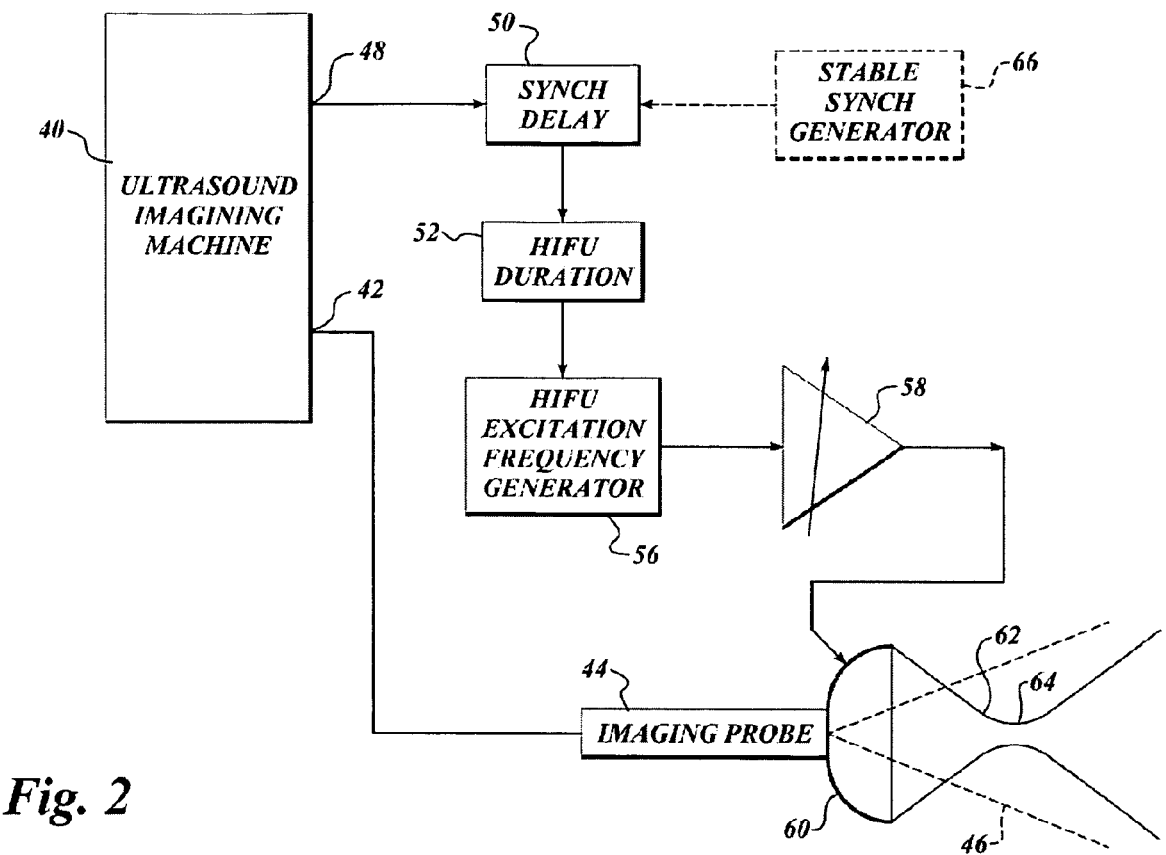

FIG. 2 illustrates a block diagram of an embodiment of the technique described herein for synchronizing the image and HIFU waves required for the simultaneous imaging and therapy in real-time. An ultrasound imaging machine 40 is one of a type that is well known to those of ordinary skill in the art and can be purchased from vendors such as Philips Medical Systems (formerly ATL Inc.), of Bothell, Wash. An imaging probe 44 that is also of a type well known to those of ordinary skill in the art is connected to ultrasound imaging machine 40 via a cable 42. Imaging probe 44 generates ultrasonic imaging pulses that propagate to the target area, are reflected from structure and tissue within the body, and are received by the imaging probe. The signal produced by the imaging probe in response to the reflected ultrasound waves is communicated to the ultrasound imaging machine through cable 42 and processed to provide a visual representation of the structure and tissue that reflected the ultrasonic imaging pulses. An imaging beam sector 46 from imaging probe 44 is identified in the Figure by dash lines. Also included is a therapeutic transducer 60. When excited, this therapeutic transducer generates HIFU waves that are focused at a particular point of interest, i.e., a treatment site within a patient's body. In FIG. 2, the path of a HIFU beam 62 is indicated by dotted lines. HIFU beam 62 narrows to a focal point 64. Those of ordinary skill in the art will recognize that position of focal point 64 relative to therapeutic transducer 60 is a function of the geometry of the therapeutic transducer and will normally depend upon the application. For example, a therapeutic transducer that will be used to apply HIFU therapy to the vascular system of a patient from within a body will have a different optimum focal point than a therapeutic transducer used to apply treatment to the vascular system from outside a patient's body. It should also be understood that therapeutic transducers having a fixed focal length can be employed, or an array of therapeutic transducers having a variable focal length can be employed. While arrays of therapeutic transducers require more sophisticated control systems, such arrays offer the benefit of enabling therapy probes having multiple focal lengths to be achieved. When a therapy probe having a fixed focal length is employed, and an initial positioning of the therapy probe does not result in the focal point of the therapy transducer being incident on the desired portion of the vascular system, the therapy probe will need to be repositioned until the focal point of the therapy transducer is properly positioned relative to the vascular system. When a therapy probe including an array of therapy transducers having variable focal lengths is employed, and the initial positioning of the therapy probe does not result in the focal point of the therapy transducers being properly positioned relative to the vascular system, the array can be controlled so as to vary the focal length of the therapy transducers until the focal point is properly positioned. Of course, there may be times when the initial positioning is so off target that the therapy probe still must be moved.

It should be noted that ultrasound imaging machine 40 differs from prior art systems in several ways, including its inclusion of a synchronization output signal 48. Preferably, ultrasound imaging machine 40 is modified to enable synchronization output signal 48 to be obtained. Because such a synchronization output signal has not been required for prior art ultrasonic imaging applications, provision of a synchronization output signal has generally not been made a standard feature in prior art ultrasound imaging machines. If a prior art imaging machine that has not been modified to provide synchronization output signal 48 is used, the synchronization output signal can instead be derived from the ultrasonic imaging signal conveyed by cable 42.

Synchronization output signal 48 is supplied to a synchronization delay circuit 50. Synchronization delay circuit 50 enables the user to selectively vary the initiation of each HIFU wave with respect to each sequence of ultrasonic imaging pulses that are generated to form an ultrasonic image. Referring to FIG. 1C, synchronization delay circuit 50 enables a user to vary the position of noise 34 in scanned field 32, so that the noise is moved away from treatment site 38, to a different portion of scanned field 32. The user is thus provided a noise-free image of treatment site 38.

A HIFU duration circuit 52 is used to control the duration of the HIFU wave. A longer duration HIFU wave will apply more energy to the treatment site. Generally, the more energy that is applied to a treatment site, the faster a desired therapeutic effect will be achieved. However, it should be noted that if the HIFU wave is too long, the duration of noise 34 as shown in ultrasound image 30 will increase and can extend into the next ultrasound imaging pulse so as to obscure treatment site 28, or may completely obscure ultrasound image 30, generating a display very similar to ultrasound image 10 in FIG. 1A. Thus, the user will have to selectively adjust HIFU duration circuit 52 to obtain a noise-free image of treatment site 38, while providing a sufficient level of energy to the treatment site to effect the desired therapeutic effect in an acceptable time.

A HIFU excitation frequency generator 56 is used to generate the desired frequency for the HIFU wave, and a power amplifier 58 is used to amplify the signal produced by the HIFU excitation frequency generator to achieve the desired energy level of the HIFU wave; power amplifier 58 is thus adjustable to obtain a desired energy level for the HIFU wave. Optionally, a stable synchronization signal generator 66 can be used to synchronize the HIFU wave to the imaging ultrasonic wave, instead of using synchronization output signal 48 from ultrasound imaging machine 40. Stable synchronization signal generator 66 can be used to provide a stable synchronizing pulse to initiate the HIFU wave, and the timing of this stable synchronizing pulse can be selectively varied until a noise-free image of the treatment site has been obtained. A drawback of using stable synchronization signal generator 66 instead of synchronization output signal 48 is that any change in the timing of the ultrasound imaging pulses, such as is required to scan deeper within tissue, will require an adjustment to stable synchronization signal generator 66 that would not be required if synchronization output signal 48 were used. The processor will be able to automatically find a stable synchronization signal using information from the movement of the noise.

It should be noted that in a clinical setting where a commercial imaging system would be used in conjunction with a HIFU system, international safety standards generally require that the electrical signals be completely isolated between the two instruments, in order to avoid potential problems with electrical leakage between the two systems. Thus, the synchronization signal pathway shown in FIG. 2 (and FIG. 8A, discussed below), will preferably include an element configured to achieve such electrical isolation. In practice, such isolation can be achieved by employing an opto-isolator, if synchronization output signal 48 is available from the imaging equipment. If no synchronization output signal 48 is available, such electrical isolation can be achieved by employing an inductive pickup coil disposed around cable 42 coupling imaging probe 44 with ultrasound imaging machine 40. Such a coil can readily pick up the imaging system's transmit pulses, and signal processing techniques can then be used to generate synchronization output signal 48.

Figure 4:
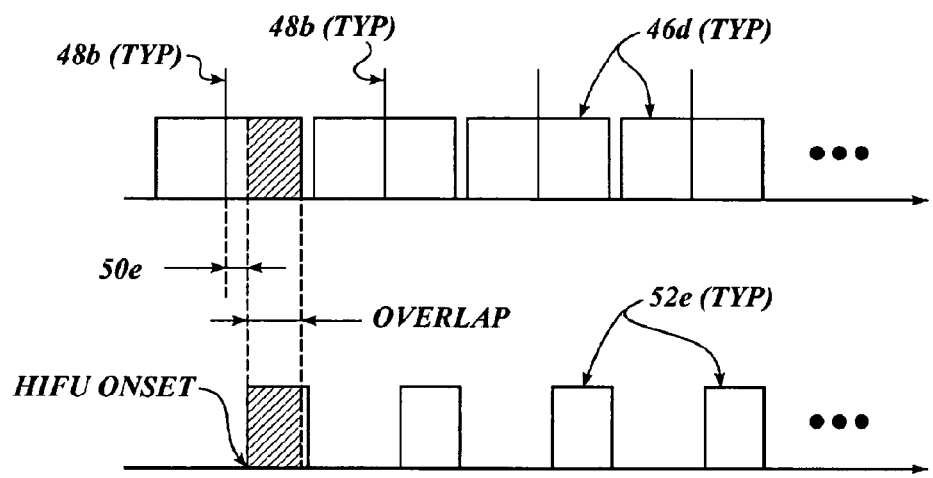

FIGS. 3A(1)-3D(4) and FIG. 4 provide further detail for the synchronization and pulsing features described herein. FIG. 3A(1) shows ultrasound imaging pulses 46a produced by imaging machine 40 and imaging probe 44 that are used to acquire an ultrasound image of a target area (such as ultrasound image 30 of FIG. 1C). A synchronization pulse 48a is shown in FIG. 3A(2). It should be noted that synchronization pulse 48a is illustrated as occurring before the generation of ultrasound imaging pulses 46a; however, the timing of synchronization pulse 48a relative to the imaging pulses is not critical, so long as it is stable. Synchronization pulse 48a merely establishes a timing reference point, from which a delay 50a (shown in FIG. 3A(3)), used for the initiation of the HIFU wave, is set such that noise from the HIFU wave in an ultrasonic image generated by imaging pulses 46a is shifted away from the image of the treatment site. Delay 50a is not fixed; instead, it is adjusted by the user until a noise-free image of the treatment site is obtained.

A HIFU duration 52a, shown in FIG. 3A(4), determines the duration of the HIFU wave. HIFU duration 52a may be very brief, as shown in FIG. 3A(4), or extended, as shown in FIGS. 3B(4) and 3C(4). An increase in the duration of the HIFU wave will cause a greater portion of an ultrasound image to be obscured by noise, and may cause the HIFU wave to interfere with the image of the treatment site. In FIG. 3A(4),HIFU duration 52a is very short, and the resulting noisy region in the ultrasound image is very small. However, a short duration HIFU wave means a correspondingly small amount of HIFU energy will be delivered to the treatment site, thus increasing the length of the treatment. A clinician must balance the length of HIFU duration needed to maintain a noise-free image of the treatment site against the time required to complete the therapy. It should be noted that as an alternative to using HIFU duration 52a to control the HIFU excitation frequency generator to variably set the duration of the HIFU wave, the HIFU excitation frequency generator itself can be adjusted to control the duration.

FIGS. 3B(1)-3C(4) similarly illustrate timing patterns that incorporate different settings for the delay relating to the initiation of the HIFU wave (delay 50b in FIG. 3B(3), and delay 50c in FIG. 3C(3)) and the delay relating to the duration of the HIFU wave (duration 52b in FIG. 3B(4), and duration 52c in FIG. 3C(4)). FIGS. 3D(1)-3D(4) illustrate a timing pattern that enables a longer duration HIFU wave (thus enabling more energy to be applied to the treatment site) to be used, while still enabling a noise-free image of the treatment site to be produced. In FIG. 3D(1), ultrasound imaging pulses 46a and 46b appear to be much shorter than in FIGS. 3A(1), 3B(1), and 3C(1), but are actually of the same duration, because the scale used in FIGS. 3D(1)-3D(4) has been significantly increased. Synchronization pulse 48a of FIG. 3D(2) is obtained and used as described above. A delay 50d in FIG. 3D(3) is set to obtain a noise-free image of the treatment site, also as described above; however, as clarified below, these synchronization pulses do not alone govern the image that is produced, because duration 52d dominates. The significant difference between FIGS. 3D(1)-3D(4) and FIGS. 3A(1)-3C(4) is that duration 52d has been significantly increased in FIG. 3D, such that a very long burst of HIFU energy is emitted, almost to the point of continuous emission. Here, the noise-free imaging occurs only every seventh image, during interrogation wave 46b. By adjusting duration 52, more or fewer images will experience interference, and therefore, various duty cycle lengths for HIFU exposure can be accommodated. It should be noted that as the number of images experiencing interference from the HIFU wave increases (here, 6 out of 7 images), the resulting image of the target area will arguably provide less real-time feedback. However, the actual time between visible images of the treatment site may be so short as to appear to the human eye as if occurring in real-time. But, at very high settings for the HIFU duration (such, for example, as would cause the HIFU wave to interfere with 99 out of 100 images of the treatment site), the advantages associated with real-time imaging of the treatment site are diminished. Thus, the HIFU duration will preferably not be set so high as to negate the benefits of real-time imaging of the treatment site and its ability to provide the clinician with immediate feedback concerning the effect of the therapy on the treatment site.

Thus, in a preferred embodiment, a portion of the ultrasound image (i.e., the region of interest (ROI) around the target tissue) would be completely free of noise from the HIFU system. This noise free ROI is achieved by synchronizing the HIFU system to the frame (i.e., a complete sequence of pulses needed to produce a single image) of the imaging system, and only activating the HIFU transducer during those portions of the frame that are not coincident with the ROI. This approach provides plenty of time for HIFU transmission, while producing an image of the ROI that is completely free of interference. FIG. 4 illustrates another timing sequence that shows the relationships between ultrasound imaging pulses 46d, a synchronization pulse 48b, a delay 50e, and a HIFU duration 52e. In this timing sequence, synchronization pulse 48b occurs during the ultrasound imaging pulses 46d, rather than preceding the ultrasound imaging pulses, as shown in FIGS. 3A-3D. As noted above, the position of each synchronization pulse 48b relative to the ultrasound imaging pulses is not critical, since delay 50e is adjusted to shift the noise away from the image of the treatment site. Again, the duration of the HIFU wave (and thus, the energy applied to the treatment site) is varied either by adjusting duration 52e, as shown in FIG. 4, or by adjusting the HIFU excitation generator.

Imaging of HIFU Focal Point

It will often be important for a clinician to be able to confirm that the focal point of a HIFU transducer is directed at a desired treatment site before initiating HIFU therapy. It has been determined that if the energy level of a HIFU transducer is reduced to a level less than that which would cause damage to tissue, the focal point of the HIFU transducer will still be evident within the target area displayed in the image developed from the reflected ultrasound signal produced and received by the ultrasound imaging transducer. The focal point will appear as a bright spot in the displayed image that rapidly fades over time. Thus, before administering a HIFU therapeutic effect, it is possible for a clinician to move the HIFU transducer as necessary to shift the focal point to a desired treatment site in the target area being imaged by the ultrasound imaging transducer and to see the focal point in the image as a bright spot that moves as the position of the HIFU transducer is changed. Only after the focal point is positioned on a desired treatment site will the clinician increase the energy of the ultrasound pulses produced by the HIFU transducer to a level sufficient to achieve the desired therapeutic effect, e.g., to a level sufficient to necrose tissue, to cause hemostasis, or to otherwise treat a neural structure by thermal and mechanical effects. It should be noted that the ultrasound imaging transducer is not receiving the ultrasound signal produced by the HIFU transducer that is reflected by the tissue, but instead, is imaging the effect of the change in echogenicity of the tissue caused by the relatively low energy ultrasound burst produced by the HIFU transducer. This technique can be used with any of the HIFU based therapy methods discussed herein.

A further advantage of this technique for imaging the focal point of a HIFU transducer can be achieved by storing the image of each successive treatment site, which will appear as a bright area in the image produced by the ultrasound imaging transducer system. For example, a storage type display, which is readily available, can be used for this purpose. By storing the image of each treatment site to which the HIFU therapy has previously been administered during a current session, it is possible for a clinician to target spaced-apart treatment sites in a target area, thereby ensuring the HIFU therapy has been administered to all of the desired portion of a tumor or other structure in the patient's body. Since each previous treatment site will be visible in the image, it will be apparent that a desired pattern of treatment sites can readily be laid down over the tumor or other structure of interest. The change in echogenicity caused by a relatively high energy therapeutic HIFU wave will be brighter and persist longer in the display, enabling the clinician to easily distinguish between a current prospective focus point for the next treatment site (produced using the low energy pulse) and previous treatment sites to which the higher energy HIFU therapy has already been administered.

Exemplary Imaging and Tracking Systems

In FIG. 8A, a block diagram is illustrated for a system 200 that enables imaging of a target area in 3D and storing of the locations of treatment sites to which the HIFU therapy has been administered in the 3D image as a HIFU therapy session proceeds. The system includes a 3D image data processor and display 202, an image acquisition section 204, a magnetic field sensor 206, a magnetic field generator 208, and six-dimensional (6D) electronic processing circuitry 210. The latter three components are employed to track the imaging target area and the HIFU focal point as they are redirected in the 3D space and are part of a 6D measurement system (i.e., three spatial coordinates for the 3D orthogonal axes and three angles of rotation around these three orthogonal axes). A 6D measurement system is commercially available from Ascension Technology, of Burlington, Vt. This 6D measurement system uses 6D electronic processing circuitry 210 and magnetic field generator 208 to produce time sequential orthogonally oriented magnetic fields covering an exemplary area indicated in the Figure by the dash line that encompasses the region of magnetic field. Magnetic field sensor 206 is mounted on a combined imaging and HIFU therapy probe 212 in a fixed manner relative to imaging and HIFU transducers 214. The magnetic field sensor detects the magnetic field strength in 3D sequentially produced by the magnetic field generator. The 6D electronic processing circuitry uses the information from the magnetic field sensor and the known magnetic fields that were produced to compute the 3D position and the three angular orientations around the three orthogonal axes of the magnetic field sensor (and thus, of the combined imaging and HIFU therapy probe) with respect to the magnetic field generator, yielding the 6D information. The 6D information is supplied to 3D image data processor and display 202 at a rate sufficient to enable movement of the magnetic field sensor to be tracked in the displayed 3D image of the target area. With information derived from calibrating system 200 with the imaging probe, the position of the target area and the HIFU transducer focal point can be related to a 3D spatial point, so long as magnetic field sensor 206 is within the range of the magnetic field produced by magnetic field generator 208. 3D image data processor and display 202 also receive ultrasound image information from an ultrasound imaging machine 216 through image acquisition section 204. It uses this information to develop and display 3D information. An ultrasound imaging machine 216 provides the synchronization signal to a HIFU control and electrical energy generating system 218, as discussed above. The remaining component in FIG. 8A is a physiological information acquisition section 220, which enables synchronization of the imaging and HIFU therapy with physiological activity, such as respiration or cardiac activity (provided by an electrocardiogram system—not shown). Use of the physiological information avoids problems associated with movement of the patient's body due to physiological activity. For example, 3D imaging and HIFU therapy can be controlled so that they are implemented only at the end of expiration in the respiratory cycle, since motion of the patient is more repeatable at that part of the cycle than at mid inspiration. A physiological sensor such as a respiration detector (not shown), which is well known in the art, can provide the information for this section of the system.

While system 200 has been described in conjunction with a single probe that includes both an imaging transducer and a therapy transducer, those of ordinary skill in the art will readily recognize that system 200 can be modified to track the positions of separate imaging probes and therapy probes.

Yet another aspect of the concepts disclosed herein is directed to a system and method that enable free-hand registration of the imaging and therapy probes, which can be employed to target portions of the vascular system for HIFU therapy. FIG. 8B schematically illustrates a system 450 that facilitates such free-hand registration. System 450 includes a HIFU therapy probe 452, an ultrasound imaging probe 456, a tracking system 454, and a display 460. It should be understood that any type of HIFU therapy probe (configured for internal or external use), and any type of ultrasound imaging probe (configured for internal or external use), can be used in connection with system 450. Instead of using a physical or mechanical frame to maintain a spatial relationship between the HIFU therapy probe and the ultrasound imaging probe, system 450 relies on tracking system 454 to ensure that the spatial relationship between the HIFU therapy probe and the ultrasound imaging probe enables the focal point of the HIFU therapy probe to be visualized in the imaging plane generated by the ultrasound imaging probe. Tracking system 454 includes a processor that is able to keep track of the spatial relationship between the ultrasound imaging probe and the HIFU therapy probe. Such tracking systems are commercially available and can be obtained from companies such as Ascension Technology, of Milton, Vt. Tracking systems for medical instruments are available based on several different technologies, including acoustic, light, and magnetic based tracking systems, any of which could be used to implement tracking system 454. Magnetic based tracking systems (e.g., the Ascension PC BIRD™) that could be used for medical instruments are available from Mind Flux of Roseville, Australia.

System 450 functions as follows. HIFU therapy probe 452 and ultrasound imaging probe 456 are positioned relative to a patient 458. The clinician can view an image 462 on display 460. Image 462 includes a representation of patient 458, and the relative locations of ultrasound imaging probe 456 and HIFU therapy probe 452. Preferably, image 462 will include a visual representation of the imaging plane provided by ultrasound imaging probe 456, and the HIFU beam generated by HIFU therapy probe 452. The clinician can determine from image 462 whether ultrasound imaging probe 456 and HIFU therapy probe 452 are properly aligned, so that the focal point of the HIFU beam can be visualized in an image provided by the ultrasound imaging probe. If the probes are not properly aligned, image 462 will provide the clinician a reference for determining how to reposition one or both of ultrasound imaging probe 456 and HIFU therapy probe 452, so that the focal point of the HIFU beam can be visualized in the ultrasound image. Depending on the size of display 460, the ultrasound image provided by ultrasound imaging probe 456 can be displayed with image 462, or a separate display can be provided to display the ultrasound image generated by ultrasound imaging probe 456. The astute observer will recognize that image 462 corresponds to FIG. 10A, which is described in greater detail below.

FIG. 8C is an enlarged view of display 460, including an image 463. The relative positions of ultrasound imaging probe 456, patient 458, and HIFU therapy probe 452 are presented in image 463. An image plane 466 provided by ultrasound imaging probe 456, a HIFU beam 468 provided by HIFU therapy probe 452, and a focal point 464 can be visualized in image 463. An optional message 470 informs the clinician that the probes are not properly aligned, which is apparent, because imaging plane 466 and beam 468 do not overlap, and further, because focal point 464 does not lie within image plane 466. While monitoring display 460 and image 463, the clinician can change the relative positions (one or both) of ultrasound imaging probe 456 and HIFU therapy probe 452, until focal point 464 lies within imaging plane 466.

It should be noted that image 463 is a two-dimensional (2D) image, and those of ordinary skill in the art will readily recognize that even if the HIFU beam and the imaging plane overlap in two dimensions, they may not overlap in three dimensions. When image 463 indicates that the imaging plane and the HIFU beam overlap, a clinician can view the ultrasound image provided by the ultrasound imaging probe, to determine whether the focal point of the HIFU beam can actually be visualized in the ultrasound image. If not, an indication is provided that the spatial relationship and orientation between the imaging plane and the HIFU beam are not properly aligned, and the clinician can further manipulate the relative positions of the imaging probe and/or the HIFU therapy probe, until the focal point of the HIFU beam both overlaps the imaging plane in image 463 and can be visualized in the ultrasound image provided by the ultrasound imaging probe. It should also be understood that tracking system 454 can provide additional images from different perspectives (or image 463 can be rotated by tracking system 454) to provide feedback to a clinician indicating the direction in which the ultrasound imaging probe and/or the therapy probe should be manipulated, so that the HIFU beam can be visualized in the image provided by the ultrasound imaging probe.

System 450 offers several advantages, including ease-of-use, the ability to visualize complex treatment strategies, and the ability to visualize complex vascular system geometries.

Advantage of Simultaneous, Real-Time Imaging

Major advantages to real-time imaging of therapeutic HIFU while it is being applied are: (1) the HIFU treatment can be stopped when a therapeutic produced lesion has grown to the point at which it just is beginning to extend beyond the desired treatment site, and the HIFU focal point can then be repositioned to another treatment site and reactivated; (2) the focal point of the HIFU wave can be observed in the image due to changes in the echogenicity of the tissue at the focal point, which are apparent in the images of the target area, providing an instant feedback that can enable a clinician to adjust the focal point onto a desired treatment site; (3) the HIFU focal point can be adjusted during the administration of the HIFU therapy to compensate for tissue movement within the patient's body due to breathing or for other reasons; (4) real-time visualization of a treatment site is very reassuring to the medical therapist, in confirming that the HIFU energy is being applied to the correct position (and that healthy tissue is not being damaged); (5) the combined imaging and therapeutic treatment can be accomplished much faster than in the past, when it was necessary to render treatment, stop the treatment, image the site, and then resume the treatment; and, (6) it enables the clinician to administer the HIFU therapy in a desired pattern of treatment sites so that, for example, a matrix of blood vessels supplying nutrients in or to a tumor can be treated to inhibit blood flow to the tumor, or to de-bulk the tumor without treating all of the tumor. Further details of how each of these advantages are achieved are discussed below.

Figure 6:
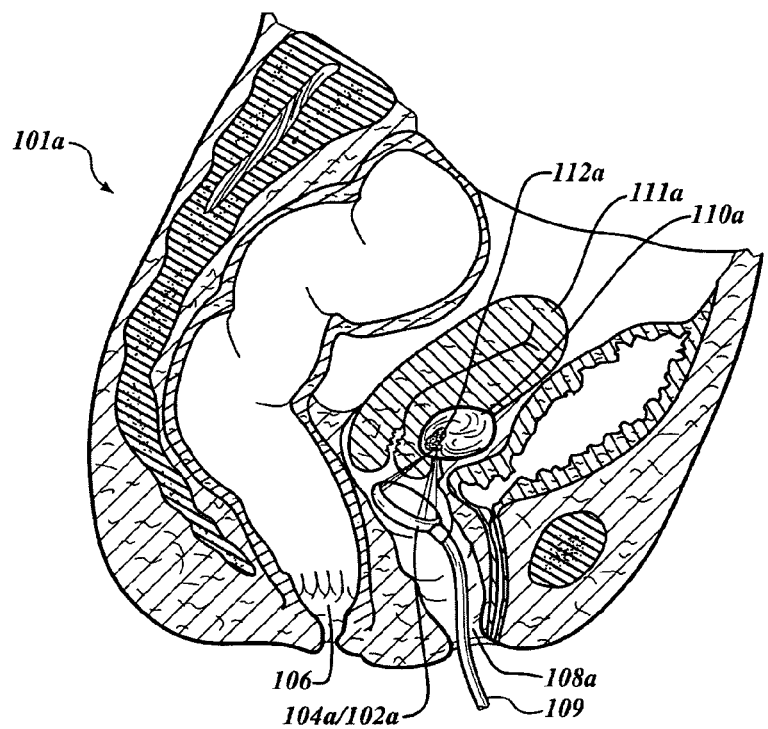
FIG. 6 is a schematic view of a vaginal probe that includes both imaging and therapeutic ultrasonic transducers being used for the simultaneous imaging and treatment of a tumor in a female reproductive system.
Figure 7:
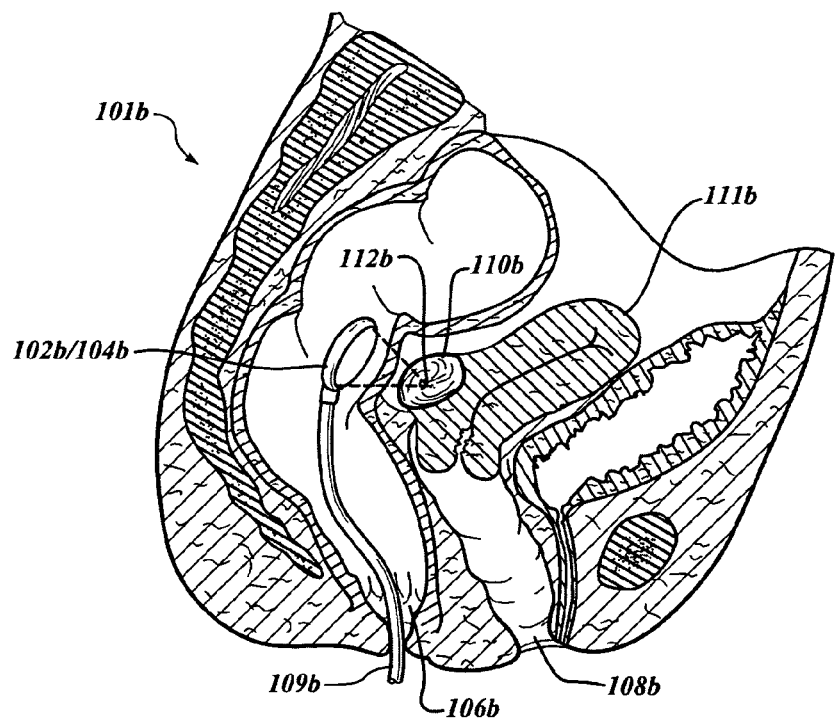
FIG. 7 is a schematic view of a rectal probe that includes both imaging and therapeutic ultrasonic transducers being used for the simultaneous imaging and treatment of a tumor in a female reproductive system, where the HIFU beam passes through the rectal wall, into the uterine cavity.

FIGS. 5-7 illustrate how a variety of different configurations of HIFU transducers and imaging transducers can be used to simultaneously provide real-time imaging and therapy to an internal treatment site within a patient's body. It is expected that HIFU therapy with real-time imaging can be beneficially employed to treat a variety of disease conditions. In particular, it is envisioned that HIFU therapy can, as a noninvasive alternative to uterine artery embolization for the treatment of uterine fibroids, particularly benefit from real-time imaging, since ultrasonic imaging is widely used in association with medical evaluation of the female reproductive system.

In FIG. 5A, both a HIFU transducer 102 and an imaging transducer 104 are disposed external to the patient's body. The reflected ultrasound waves received by imaging transducer 104 are used to generate an ultrasound image 100 shown in FIG. 5B. In FIG. 5A, the HIFU is being used to treat vascular structures within a tumor 110 on a uterus 111 of the patient, which provide blood flow to the tumor. Imaging transducer 104 is positioned so that tumor 110 and the vascular structure associated with the tumor are clearly displayed in ultrasound image 100. Also visible in ultrasound image 100 is a cross section of a rectum 106. HIFU transducer 102 is being used to destroy vascular structures within tumor 110 that provide nutrients to the tumor. The HIFU generates a lesion 112, which can be seen in both the cross section of the body and in ultrasound image 100. Lesion 112 is intended to represent an exemplary blood vessel occlusion generated by HIFU therapy.

FIG. 6 illustrates an exemplary embodiment in which a HIFU transducer 102a and an imaging transducer 104a have been combined on a vaginal probe 109. Vaginal probe 109 has been inserted into a vaginal canal 108a and positioned to enable imaging transducer 104a to be used in generating an ultrasonic image of a tumor 110a. Once tumor 110a has been located, HIFU transducer 102a is focused on a selected portion of the vasculature of tumor 110a to which the clinician desires to administer the HIFU therapy to generate a lesion 112a, to occlude blood flow within the tumor. The HIFU therapy is used to destroy the tumor by causing lesions of the blood vessels supplying oxygen and nutrients to the tumor, similar to lesion 112a, so that the tumor withers away.

FIG. 7 illustrates an exemplary rectal probe 109a, which incorporates a combination of a therapy transducer 102b and an imaging transducer 104b. Rectal probe 109a has been inserted into a rectum 106b of a patient, and the imaging transducer is being used to locate a tumor 110b. Once tumor 110b has been located, therapy transducer 102b is focused on the desired portion of the vasculature supplying nutrients to the tumor, and HIFU therapy is administered to a treatment site 112b, until the desired therapeutic effect is achieved. Note that tumor 110b is in uterus 111, and the HIFU beam passes through the rectal wall, into the uterine cavity.

Useful Therapy Probes, Imaging Probes, and Frames

The technique described herein for treating a portion of the vascular system using HIFU therapy can be implemented using a variety of different imaging probes and ultrasound therapy probes. Several different types of imaging technologies can be beneficially employed as alternatives to ultrasound imaging. Exemplary imaging technologies thus include magnetic resonance imaging, magnetic resonance angiography, computed tomographic angiography, ultrasound imaging, and Doppler ultrasound imaging.

As discussed above in detail, if ultrasound imaging is used as an imaging technology, synchronizing the ultrasound imaging waves to the HIFU therapy waves can ensure that the ultrasound image of the target area is not rendered unusable by noise introduced into the ultrasound image by the highly energetic HIFU waves. With respect to the use of ultrasound imaging, combination probes, where the therapeutic ultrasound transducer and the imaging ultrasound transducer are provided on a single probe, are particularly useful if the combination probe is intended to be introduced into a body cavity. In such combination probes, the spatial relationship between the imaging transducer and the HIFU transducer is generally static, because both the scanning transducer and the HIFU transducer are combined in a single instrument. Movement of the probe will generally not move the focal point of the HIFU transducer out of the imaging plane of the scanning transducer, because both transducers are part of the combination probe. Some combination probes are based on prior art imaging probes to which a therapy head has been retrofitted, while other combination probes integrate the imaging and therapy transducers into a single new device.

The techniques described herein can also be implemented using separate imaging probes and therapy probes. One advantage of using separate imaging probes and therapy probes is that ultrasound imaging probes are relatively ubiquitous, and many medical offices already have access to ultrasound imaging probes and ultrasound imaging systems. Thus, the ability to simply purchase an ultrasound therapy probe to enable image guided HIFU therapy of the vascular system to treat undesired tissue masses will likely reduce the cost of implementing this new treatment method. When separate imaging probes and therapy probes are employed, it may be beneficial to utilize a frame or bracket to maintain a desired spatial orientation between the imaging probe and the therapy probe, particularly when the tracking systems described above are not employed. When such a frame is employed, before therapy is initiated, the clinician will verify that the focal point of the therapy probe will lie within the image plane of the imaging probe. This step can either be established geometrically (by understanding the beam geometry of the ultrasound imaging probe and the HIFU therapy probe, and then ensuring that the probes are positioned so that the beams overlap), or it can be empirically established. An icon can be added to an ultrasound image generated by the imaging probe to represent the predicted location of the focal point of the HIFU beam. The clinician can then manipulate the position of the combined instruments until the icon overlies the desired treatment point in the ultrasound image. The position of the icon verifies that the focal point of the HIFU transducer will coincide with the desired treatment site. As discussed in greater detail herein below, the clinician can then employ one of several additional techniques to verify that the focal point is indeed properly positioned before initiating therapy, if so desired.

HIFU Therapy Applied to the Vascular System to Treat Unwanted Tissue

One feature of the present approach is that it causes necrosis or reduction of unwanted tissue by selectively targeting vascular structures that provide nutrients to the unwanted tissue, rather than directly targeting the unwanted tissue itself. For example, a tumor can be treated by identifying the major vascular structures providing blood flow to the tumor, and once identified, those structures can be destroyed, damaged, or occluded using HIFU. As a result of destroying/occluding the vasculature structure(s) associated with a tumor, the tumor tissue is denied nutrients and oxygen that were previously conveyed by blood flowing through the vasculature structure(s), and the unwanted tissue eventually dies.

FIG. 9 shows a flowchart 300 that indicates a sequence of logical steps to perform HIFU therapy on the vascular system to treat undesired tissue. As noted above, such therapy can be used to de-bulk or eliminate tumors by denying nutrients provided by blood flow. In a block 302, an image of the vascular structures providing blood flow to the unwanted tissue is obtained. In an exemplary embodiment, Doppler ultrasound imaging is employed, although it must be emphasized that the techniques described herein are not intended to be limited either to a specific type of ultrasound (as indicated in a block 312) or to a specific type of medical imaging. As noted above, alternative medical imaging technologies can be employed to obtain an image of the vascular structures associated with unwanted tissue. Those imaging technologies include, but are not limited to, magnetic resonance angiography (as indicated by a block 308), magnetic resonance imaging, and computed tomographic angiography (as indicated in a block 310). Furthermore, it is likely that additional alternative imaging technologies may be developed in the future, and when appropriate, such imaging technologies may also be employed to visualize vascular structures associated with unwanted tissue, and thus to enable specific vascular structures providing nutrients to the unwanted tissue to be selectively targeted.

In a block 304, a particular portion of the vascular system associated with the unwanted tissue is selected as a treatment site. Preferably a clinician will exercise care in selecting an appropriate treatment site, to ensure that the treatment site selected does not provide blood flow to vital organs or healthy tissue that is to remain unaffected by the treatment. The vascular structures selected as a treatment site can be fully or partially encompassed by the undesired tissue, or can be being spaced apart from the undesired tissue. Where the vascular structure is not encompassed by the treatment site, the clinician will need to pay particular attention to ensuring that occlusion of the vascular structure will not detrimentally affect vital organs or healthy tissue, which should not be damaged by the therapy. Those of ordinary skill in the art will recognize that the particular vascular structures selected as a treatment site will be a function of the type and location of the undesired tissue being treated. An exemplary implementation of this technique will be its use as an alternative to uterine artery embolization (an invasive therapy used to de-bulk uterine fibroids by occluding blood vessels providing nutrients to the fibroid). In such an implementation, the treatment site will be branches of the uterine artery primarily servicing the fibroid itself. Thus, the treatment sites will generally be located relatively close to the uterine fibroid, or within the uterine fibroid, to prevent interruption of blood flow to other portions of the uterus. Particularly because of the potential negative implications of occluding blood flow to healthy tissue or vital organs, those of ordinary skill in the art will readily recognize that the step of choosing an appropriate treatment site must be carried out very carefully. The treatment site will therefore normally be selected to maximize a beneficial therapeutic effect, while minimizing any undesired effects. Thus, selection of a treatment site will generally be based not only on a thorough knowledge of anatomy and the vascular system, but also on a careful review of the particular patient's vascular system in the affected area, to help ensure that the selected treatment site does not provide blood flow to a vital organ or other tissue that should not be damaged.

In a block 306, a HIFU transducer (i.e., a HIFU therapy probe) is positioned such that the focal region (or focal point) of the therapy transducer is incident on the treatment site selected, and HIFU is administered to disrupt blood flow at the selected treatment site. As noted above, this disruption of the blood flow will deny or reduce the flow of nutrients provided to the unwanted tissue, which will lead to a de-bulking of the unwanted tissue mass, or in some cases, the complete elimination of the unwanted tissue. A more detailed discussion of the steps involved in an exemplary technique is provided below.

FIG. 10A illustrates an exemplary use of HIFU therapy applied to the vascular system of a patient in accord with the techniques described herein to treat undesired tissue 99. In a HIFU therapy probe 65, an acoustic coupling 67 is attached to a therapy transducer 68 mounted to a handle 70. A lead 72 connects the transducer to a power supply (not shown). In FIG. 10A, probe 65 is being used to apply HIFU to a vascular structure 82 proximate to a dermal layer 76 of a patient (not otherwise shown). While many different acoustic transducers are suitable for HIFU applications, typical HIFU transducers produce a generally conical-shaped beam 74 that has a substantially smaller, generally elliptical focal region 78. When probe 65 is positioned so that focal region 78 is coincident with vascular structure 82, and therapy transducer 68 is energized, HIFU therapy (i.e., partial or complete occlusion) of vascular structure 82 is achieved.

It should be understood that vascular structure 82 is illustrated in this Figure simply as a schematic representation of an exemplary blood vessel and is not intended to represent any specific blood vessel. It should also be understood that suitably configured HIFU therapy probes for treating vascular structures could be used inside a patient's body (inserted either via a body cavity or transdermally through an incision) and are not limited to external use. The use of an external HIFU therapy probe or a HIFU therapy probe configured for insertion into a body cavity is likely preferred to inserting HIFU therapy probes into the body via an incision, which is more invasive and likely to cause infection.

An important component in any type of ultrasound therapy system is the mechanism for coupling the acoustic energy into the tissue. Good acoustic coupling is necessary to efficiently transfer the ultrasound energy from the transducer to the treatment site. The ideal acoustic coupler is a homogenous medium that has low attenuation and acoustic impedance similar to that of the tissue being treated. Due to its desirable acoustic transmission characteristics, water has commonly been used as the coupling medium in many therapeutic applications of ultrasound.

Several different types of acoustic couplings are known. Acoustic viscous coupling gels can be applied over the distal end of the probe and on the patient's skin (or tissue layer in a body cavity) to facilitate acoustic coupling. Water is an excellent acoustic coupling medium, and water-filled sacks or envelopes are often disposed between an acoustic transducer and the skin layer to facilitate acoustic coupling. While the use of such aqueous-filled membranes is well known, there are some disadvantages to using aqueous-filled membranes for acoustic coupling. These disadvantages include a requirement for degassing the aqueous solution (the presence of gas bubbles will significantly impede transmission of the ultrasound waves), sterilization concerns, and containment issues. Hydrogels are solids having a particularly high water content, and are efficient coupling media for diagnostic ultrasound. Hydrogels are hydrophilic, cross-linked, polymer networks that become swollen by absorption of water. The high water content and favorable mechanical properties of hydrogels have made them attractive for a wide range of biomedical applications, including soft contact lenses, maxillofacial reconstruction, burn dressings, and artificial tendons. Since hydrogels consist mostly of water, they inherently have low attenuation and acoustic impedance similar to tissue. They can be formed into rigid shapes and have relatively low material costs. Unlike the ultrasound transmission gels typically used for diagnostic scans, hydrogels can have consistencies similar to soft rubber, and can be formed into relatively rigid, 3D shapes. In one preferred embodiment, acoustic coupling 67 is implemented as a hydrogel coupling. It should be understood, however, that acoustic coupling 67 can also be implemented as a viscous ultrasound transmission gel or an aqueous-filled membrane.

Therapy transducer 68 has a fixed focal length. That is, focal region 78 is separated from therapy transducer 68 by a fixed distance (absent any interactions with matter that would tend to deflect the acoustic waves traveling to focal region 78). Yet, this approach is not limited to the use of fixed focal length acoustic transducers, and phased arrays of acoustic transducers having variable focal lengths can also be employed, as noted above. However, a fixed focal length acoustic transducer can be used to achieve a robust, relatively simple, and useful HIFU therapy probe. In applications where a fixed focal length acoustic transducer is used for HIFU therapy, acoustic coupling 67 can be employed to control the position of focal region 78 relative to the patient. If a relatively thicker acoustic coupling 67 is employed, focal region 78 will be disposed closer to dermal layer 76, while if a relatively thinner acoustic coupling 67 is employed, the focal region will penetrate further below the dermal layer and deeper into the subcutaneous tissue. Thus, the thickness of acoustic coupling 67 can be used to control the position of the focal region relative to a patient's tissue. As noted above, hydrogels can be formed into relatively rigid, 3D shapes and are inexpensive. Thus, by providing a plurality of hydrogel couplings of different thicknesses, a selected thickness hydrogel coupling of the plurality of such couplings can be used to enable HIFU therapy probe 65 to deliver HIFU to treatment sites disposed at various distances from dermal layer 76. This effect is readily apparent in FIG. 10B, in which an acoustic coupling 67a replaces acoustic coupling 67 of FIG. 10A, and focal region 78 now coincides with a different portion of vascular structure 82. In FIG. 10B, an ultrasound imaging probe 84 generates an image plane 86. Focal region 78 lies within image plane 86, so that focal region 78 can be visualized in an ultrasound image provided by image ultrasound imaging probe 84 during therapy, using the synchronization method described above. Again, however, it should be understood that the techniques described herein are not limited to the use of ultrasound as an imaging technique, and that other types of imaging probes can also be used, generally as described above.

An additional difference between the HIFU therapy of the vascular structure schematically illustrated in FIGS. 10A and 10B is that in FIG. 10A, the vascular structure being targeted is encompassed within undesired tissue 99a, while in FIG. 10B, the vascular structure being targeted lies outside undesired tissue 99b. Thus, it should be recognized that the techniques described herein can be applied to vascular structures both within an unwanted tissue mass and external to an unwanted tissue mass.

As discussed above, when separate imaging and HIFU therapy probes are employed, it will likely be desirable to use a frame to couple the imaging probe to the HIFU therapy probe, so that the positions of the probes relative to each other remain fixed during therapy/imaging. In FIG. 10C, both a HIFU transducer 102 and an imaging probe 104 are disposed external to the patient's body. The imaging probe is used to generate an image of vascular structure associated with a tumor 110 on a uterus 111 of the patient. A frame 350 is used to control the relative spatial orientation of HIFU transducer 102 and imaging probe 104. As described in detail above, once the desired spatial orientation is obtained, such that the focal point of the HIFU beam can be visualized in the ultrasound image, the frame maintains the spatial orientation between the HIFU transducer and the imaging transducer, so that movement of the patient, or the frame, does not cause the focal point of the HIFU beam to move out of the imaging plane provided by the imaging transducer. Frame 350 includes a plurality of adjustable members, which enables a user to adjust the relative positions of HIFU transducer 102 and imaging probe 104.

FIG. 11 shows a flowchart 390 that indicates a sequence of logical steps to perform HIFU therapy on the vascular system to treat undesired tissue. As noted above, such therapy can be used to completely or partially occlude blood vessels providing nutrients to undesired tissue, to de-bulk or destroy the undesired tissue. In a block 392, a massive undesired tissue, such as a tumor or a uterine fibroid, is selected. In a block 394 one of the imaging technologies described above is used to image the vascular structure associated with the undesired tissue or to identify vascular structures (i.e., a treatment site) for administering HIFU therapy. The particular treatment site will be a function of the configuration of the vascular structure and the undesired tissue. Those of ordinary skill in the art will readily recognize that the step of choosing an appropriate treatment site must be carried out very carefully, e.g., to maximize a beneficial therapeutic effect, while minimizing any undesired effects.

In a block 395, the therapy probe is positioned such that the focal region (or focal point) of the therapy transducer is incident on the treatment site selected (i.e., on a portion of the vascular structure providing blood flow to the undesired tissue, which as described above, may be disposed within the undesired tissue, or may be external to the undesired tissue). Determining where the therapy probe should be positioned will be a function of the anatomical position of the vascular structure and the focal length of the therapy transducer. Verification of the anatomical position of the treatment site can be carried out in a pre-therapy exam using imaging technologies such as ultrasound or MRI. Based on the identified location of the treatment site, and the known focal length of the therapy transducer, an optimal position for the therapy probe can be fairly accurately established.

In a block 396, the accuracy of the positioning of the therapy probe relative to the treatment site (and more importantly, the position of the focal point relative to the treatment site) is evaluated to verify that the therapy probe is properly positioned. As described in detail below, several different techniques can be used to verify that the therapy probe, and the focal point of the therapy transducer are properly positioned relative to the treatment site. Once the proper positioning of the therapy probe has been verified, in a block 398, the therapy transducer is energized to provide HIFU therapy to the portion of the vascular system corresponding to the selected treatment site. In a decision block 400, the treatment site is evaluated to determine whether the desired therapeutic effect has been achieved. Such an evaluation preferably includes imaging the treatment site during therapy using an imaging technology capable of determining whether occlusion of the target site has been achieved (to achieve real-time image guided therapy). Alternatively, the imaging can be performed post therapy. Real-time image guided therapy is preferred, because the clinician may then monitor the treatment site in real-time and halt the therapy if the thermal and mechanical effects (such as lesion formation) are beginning to extend beyond the identified treatment site. Thus, real-time image guided therapy provides the clinician the assurance that therapy can be halted if the therapeutic effect desired has been achieved and to avoid damage to tissue extending beyond the selected treatment site.

As noted in the details of block 396 (shown in FIG. 11), several different techniques can be used to verify that the focal point of the HIFU transducer coincides with the selected treatment site in the vascular system. In a block 396a, a combination of imaging and HIFU beam geometry are used to verify that the focal point properly coincides with the selected treatment site. As indicated above, the focal length of a HIFU transducer is a well-defined parameter. Referring now to FIG. 10B, if the relative positions of therapy probe 65 and imaging probe 84 are known, the relative position of focal region 78 within imaging plane 86 can be determined. An icon can be introduced into the ultrasound image provided by imaging probe 84 to indicate the anticipated position of focal region 78 (based on the relative positions of the therapy probe in the imaging probe, and the known characteristics of the focal length). If the ultrasound image from imaging probe 84 indicates that focal region 78 does not properly coincide with the selected treatment site, therapy probe 65 and imaging probe 84 can be moved in concert until the icon corresponding to the predicted position of the focal region properly coincides with the selected treatment site. If the therapy transducer and imaging transducer are implemented as a single probe, any movement of the imaging transducer will result in a corresponding movement of the therapy transducer. If the imaging transducer and the therapy transducer are implemented as separate instruments, care must be taken so that any movement of the imaging probe is matched by a corresponding movement of the therapy probe (unless a sophisticated tracking system such as described above is used to independently track and display the positions of each probe). The desired result can be achieved by using a frame to couple the imaging probe to the therapy probe. In this event, any movement of the imaging probe used to ensure that the icon representing the focal region of the HIFU transducer coincides with the desired treatment site will result in a corresponding motion of the therapy probe. While this technique has been specifically described as using ultrasound imaging, those of ordinary skill in the art will readily recognize that MRI could be used in place of ultrasound imaging to achieve the same result.

Yet another technique for verifying that the focal point of the HIFU transducer coincides with the selected treatment site involves the use of relatively low power HIFU combined with imaging, as indicated in a block 396b. As noted above, even a relatively low power HIFU wave will change the echogenicity of the target at the focal point of the HIFU transducer. This change in echogenicity can be identified using imaging ultrasound. Thus, in this technique, the HIFU transducer is energized at a power setting selected to change the echogenicity of the treatment area at the focal point but minimize any therapeutic effects, so that if the focal point is not correctly aligned, minimal undesirable effects on non-target tissue will occur. Empirical studies have indicated that relatively low levels of HIFU will change the echogenicity of the treatment site without any other appreciable effects on non-targeted tissue (i.e., no tissue necrosis or noticeable damage). This change in echogenicity persists briefly, so that the change can be detected by using imaging ultrasound after a relatively short burst of low power HIFU has been delivered. Alternatively, the synchronization techniques described above can be used in real-time to visualize the treatment site as the low level HIFU is being delivered. Regardless of the approach used, the change in echogenicity in the ultrasound image is identified to determine whether the therapy probe is properly positioned so that the focal region coincides with the selected treatment site. If not, the therapy probe is repositioned, and an additional verification step is performed, until the change in echogenicity induced by the relatively low power HIFU burst coincides with the desired treatment site. This verification technique can be used in connection with a frame, thereby ensuring that the spatial orientation between the imaging probe in the therapy probe remained fixed, or this technique can be used in freehand registration of the probes without requiring a sophisticated tracking system, as described above.

Use of Contrast Agents to Enhance HIFU Treatment

Ultrasound contrast agents provide an effective adjuvant tool for medical procedures involving both ultrasound diagnosis and therapy. Contrast agents can be used before therapy is initiated to improve the imaging procedure used to locate particular vascular structures for treatment. Contrast agents can also be used to more readily determine the focal point of a HIFU therapy transducer while the HIFU therapy transducer is operated at a relatively low power level, so that damage to normal tissue does not occur while the HIFU transducer is being properly focused at the target location (such as a tumor) where tissue damage is desired, and the power level then increased. FIG. 12 schematically illustrates contrast agents 226 being introduced into a patient's vascular system 230 using a syringe 222 to pierce a dermal layer 228.

Before discussing the use of contrast agents in detail, it will be helpful to discuss the types of contrast agents that can be employed. Micro-bubbles serve as contrast agents for use with ultrasound, and contrast agents that readily form micro-bubbles when exposed to ultrasound energy are therefore very useful. Gas-filled contrast agents provide a large scattering cross section due to the significant difference between the compressibility of the contrast agent content (air or other gases) and the ambient surroundings of the contrast agent in the body (generally body fluids or tissue). Therefore, the interaction of ultrasound waves and a contrast agent leads to strong echo signals, resulting in enhanced hyperechogenecity of a region in the body where the contrast agent is disposed. It should be understood that contrast agents can be provided either as a liquid solution that already includes micro-bubbles when introduced into a patient's body, or as a liquid that can be induced to form micro-bubbles at a target location in a patient's body in response to ultrasound.

Many different prepared micro-bubbles solutions are commercially available for use as ultrasound contrast agents, including ECHOVIST™ (produced by Schering of Germany), ALBUNEXTM™ (Molecular Biosystems/Mallinckrodt, USA), SONAZOID™ (Amersham Health, of Oslo, Norway), and OPTISON™ (Mallinckrodt, of St Louis, Mo.). Generally, such ultrasound contrast agent preparations comprise suspensions of millions of tiny air- or gas-filled bubbles, with sizes as small as 1-10 μm. These micro bubbles are stabilized within a biodegradable shell. Without this shell, the bubbles would be stable only transitorily (for only a few seconds), because the un-stabilized micro bubbles would soon merge into larger bubbles. Besides being potentially hazardous to the patient, large bubbles have different, and less suitable, reflective properties, that are not desirable in a contrast agent.

Liquids that can be used to generate micro-bubbles in-vivo include anesthetic agents, or other blood soluble agents having a relatively high vapor pressure. Such agents will readily vaporize when exposed to the slight elevated temperatures caused by low power ultrasound. Ultrasound waves can also induce cavitation in liquids, providing another mechanism for bubble formation. Because such bubbles are formed in-vivo at an expected target site, the more transitory nature of micro-bubbles lacking stabilizing shells is not a particular disadvantage, because the bubbles will exist at the imaging site long enough for their presence to have the desired effect. Halothane, isoflurane, and enflurane (fluorinated solvents) are exemplary of high vapor pressure aesthetics, whereas methoxyflurane is exemplary of a less volatile anesthetic. It should be understood that the high vapor pressure liquid does not necessarily need to be an anesthetic. Instead, high vapor pressure anesthetics represent known materials that are regularly used in-vivo and are substances whose toxicological effects are well understood. Many other high vapor pressure liquids are known and can be beneficially employed as ultrasound contrast agents, so long as the toxicological effects of such liquids are well understood and do not pose a health risk to the patient.

Two mechanisms can be used to induce in-vivo micro-bubble formation in suitable volatile liquids. Ultrasound energy can be used to slightly heat adjacent tissue, so that the heated tissue in turn heats the volatile liquid, which volatilizes and produces the micro bubbles. If the adjacent tissue is not tissue that is to be heated in the course of administering HIFU therapy, care must be exercised that the tissue is not heated to a temperature sufficient to damage the tissue or causes necrosis. Ultrasound energy can also be absorbed by certain volatile liquids directly. If sufficient ultrasound energy is delivered to a liquid, a phenomenon referred to as cavitation occurs. Cavitation is the formation, growth, and collapse of micro bubbles. The amount of energy that is required to induce cavitation is based on the strength of the attractive forces between the molecules that comprise the liquid. The implosion of these tiny bubbles is sufficiently energetic to provide at least some of the energy required to induce further cavitation. Because cavitation is such an energetic phenomenon, care must be exercised to avoid undesirable tissue damage. The cavitation phenomenon is a function of environmental characteristics (the temperature and pressure of the liquid) as well as physical properties of the liquid (surface tension, the attractive forces holding the components of the liquid together, etc.). Empirical studies based on specific volatile liquids and ultrasound power levels, e.g., using animal models, should be conducted prior to inducing in-vivo micro-bubbles via cavitation to enhance ultrasound therapy. In general, less energetic ultrasound imaging waves will be less efficient in forming micro bubbles, because lower energy ultrasound imaging waves do not cause a sufficient temperature increase to occur. Preferably, the step of inducing volatile liquids to generate micro bubbles in-vivo will be achieved using HIFU, while simultaneously scanning the target area using conventional imaging ultrasound.

Returning now to the different ways in which ultrasound contrast agents can be employed, as noted above, ultrasound contrast agents can be used before HIFU-based therapy is initiated to locate particular vascular structures for treatment. The change in echogenicity provided by blood soluble ultrasound contrast agents (or ultrasound contrast agents that can be entrained in blood) can be used to differentiate high blood flow regions from low blood flow regions. Because tumors usually exhibit a blood flow pattern that is different than that of surrounding normal tissue, ultrasound contrast agents can enhance the visualization of tumors, thereby facilitating the identification of the target area for HIFU therapy. Furthermore, when initially administered, ultrasound contrast agents will be first carried through larger blood vessels (arteries, arterioles, veins, etc.) rather than capillaries. Thus, different vascular structures can be identified as potential targets for HIFU therapy. For example, a tumor can be treated by using ultrasound contrast agents to identify the major vascular structures providing blood flow to the tumor, and once identified, those structures can be destroyed using HIFU. As a result of destroying the vasculature structure(s) associated with a tumor, the tumor tissue is denied nutrients and oxygen that were previously conveyed by blood flowing through the vasculature structure(s) and eventually dies.

The second use of ultrasound contrast agents in connection with HIFU therapy noted above was for identifying a location for targeting the focal point of the HIFU beam. The energy delivered at the focal point of a HIFU beam can damage tissue by increasing its temperature and can cause tissue necrosis. If the focal point of the HIFU beam is not properly directed, damage to non-target tissue in a patient's body can occur. As discussed in detail above, one technique to determine the focal point of the HIFU beam is to energize the HIFU transducer at a relatively low power, such that some thermal energy is imparted to the tissue at the focal point of the HIFU beam, but so that the amount of thermal energy delivered to the non-target tissue is insufficient to cause damage or tissue necrosis. Administering HIFU to tissue at energy levels too low to cause damage will nevertheless change the echogenicity of the tissue sufficiently to cause the focal point of the HIFU beam to appear as a bright spot in an image formed using ultrasound imaging waves. While one explanation for this effect is that a change in the temperature of the tissue causes a change in echogenicity, it is also believed that a more significant factor in producing the change in echogenicity is the interaction of the pressure oscillations of the low intensity HIFU ultrasound beam within the tissue, which causes micro-bubbles to form in the tissue. This technique can be modified, so that ultrasound contrast agents are first delivered to the target area.

When volatile liquid contrast agents are present in the target area, the HIFU transducer is energized at an even lower power level (than when a contrast agent is not used). The contrast agent volatilizes to form micro bubbles, which are readily detectable using ultrasound imaging waves. Less energy is required to cause the contrast agent to form bubbles than is required to increase the temperature of tissue sufficiently to produce a detectable change in the echogenicity of the tissue (or to produce micro-bubbles in tissue that also produces a detectable change in the echogenicity of the tissue). The bubbles generated by the contrast agent will produce a substantially brighter spot in the ultrasound image than can be achieved when targeting tissue without the use of a contrast agent, and at an even lower energy level. Reduction of the HIFU energy used to determine the correct focal point position of the HIFU transducer to an even lower level than would be used without the contrast agent also ensures that the focal point of the HIFU transducer is evident in the ultrasound image produced by the imaging transducer, but without risk of damage to tissue that is not to be treated.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for using high intensity focused ultrasound (HIFU) to treat undesired tissue by damaging selected vascular regions to affect a viability of the undesired tissue, without directly targeting the undesired tissue with the HIFU, comprising the steps of:
   (a) using imaging ultrasound to visualize an appropriate treatment site associated with the vascular system of a patient to be treated, so that damage of the treatment site will negatively affect the viability of the undesired tissue, by reducing blood flow to the undesired tissue;
   (b) positioning a HIFU therapy device such that a focal point of the HIFU therapy device is directed to the treatment site;
   (c) energizing the HIFU therapy device to disrupt the vascular system at the treatment site, thereby reducing blood flow to the undesired tissue and negatively affecting the viability of the undesired tissue; and
   (d) generating a plurality of ultrasound images during HIFU therapy, such that HIFU noise does not prevent the treatment site from being visualized in the plurality of ultrasound images, an interval between sequential ultrasound images being sufficiently small such that from a user's perspective, the sequence of ultrasound images provides real-time imaging during HIFU therapy.

2. The method of claim 1, wherein the step of determining an appropriate treatment site associated with the vascular system of the patient comprises the step of producing an image in which a portion of the vascular system associated with the undesired tissue is visible, and selecting the treatment site within the portion of the vascular system associated with the undesired tissue based on the image of the portion of the vascular system, thereby enabling the HIFU therapy to be targeted at a selected vascular structure.

3. The method of claim 2, wherein the step of selecting the treatment site within the portion of the vascular system associated with the undesired tissue comprises the steps of analyzing the image to identify at least one blood vessel providing nutrients to the undesired tissue, and selecting the at least one blood vessel providing nutrients to the undesired tissue as the treatment site.

4. The method of claim 1, wherein the step of energizing the HIFU therapy device comprises the step of producing pulses of HIFU waves, further comprising the step of synchronizing the pulses of HIFU waves produced by the HIFU therapy device relative to imaging ultrasound waves used to produce the image of the portion of the vascular system associated with the undesired tissue, such that noise from the HIFU waves does not prevent visualization of the treatment site in the image.

5. The method of claim 1, further comprising the steps of:
(a) initially energizing the HIFU therapy device at a reduced energy level so as to produce a pulsed wave that is not sufficiently energetic to damage the vascular system at the treatment site, but is sufficiently energetic to produce a change in an echogenicity at the treatment site, a focal point of the HIFU therapy device being visually apparent in the image due to the change in the echogenicity;
(b) as required, moving the focal point of the HIFU therapy device until the focal point coincides with the treatment site; and
(c) increasing the energy level of the HIFU therapy device to generate HIFU waves with sufficient energy to damage the vascular system that is coincident with the focal point of the HIFU therapy device.

6. The method of claim 1, wherein the undesired tissue is a uterine fibroid, and wherein the step of determining an appropriate treatment site associated with the vascular system of the patient comprises the step of selecting at least a portion of a uterine artery supplying the uterine fibroid with nutrients as the treatment site.

7. The method of claim 1, wherein the step of determining an appropriate treatment site associated with the vascular system of the patient comprises the step of selecting a vascular structure that is not encompassed within the undesired tissue.

8. The method of claim 1, wherein the step of determining an appropriate treatment site associated with the vascular system of the patient comprises the step of selecting a vascular structure that is encompassed within the undesired tissue.

9. A method for using high intensity focused ultrasound (HIFU) to provide therapy to damage undesired tissue by selectively targeting a treatment site corresponding to a portion of a vascular system of a patient associated with supplying nutrients to the undesired tissue, the treatment site being spaced apart from a HIFU therapy device that provides the therapy, comprising the steps of:
(a) determining an appropriate treatment site associated with the vascular system of the patient to be treated to reduce an amount of blood flow that supplies nutrients to the undesired tissue;
(b) positioning the HIFU therapy device such that a focal point of the HIFU therapy device is directed at the treatment site, but does not directly target the undesired tissue;
(c) verifying that the focal point of the HIFU therapy device is properly positioned relative to the treatment site, and if not, repositioning the HIFU therapy device until the HIFU therapy device is properly positioned relative to the treatment site, wherein the step of verifying that the focal point of the HIFU therapy device is properly positioned relative to the treatment site comprises the steps of:
  (i) using ultrasound imaging to obtain an ultrasound image of the treatment site; and
  (ii) energizing the HIFU therapy device at a power level that is insufficient to induce substantial damage at the treatment site, but is sufficient to enable the focal point to be visualized in the ultrasound image; and
(d) energizing the HIFU therapy device to damage the vascular system at the treatment site to reduce the amount of blood flow to the undesired tissue, so that the undesired tissue is damaged by a reduction in the blood flow to it.

10. The method of claim 9, further comprising the step of generating a plurality of ultrasound images during HIFU therapy, such that HIFU noise does not prevent the treatment site from being visualized in the plurality of ultrasound images, an interval between sequential ultrasound images being sufficiently small such that from a user's perspective, the sequence of ultrasound images provides real-time imaging during HIFU therapy.

11. The method of claim 9, wherein the undesired tissue is a uterine fibroid, and wherein the step of determining an appropriate treatment site associated with the vascular system of the patient comprises the step of selecting at least a portion of a uterine artery supplying the uterine fibroid with blood, as the treatment site.

12. The method of claim 9, wherein the step of verifying that the focal point of the HIFU therapy device is properly positioned relative to the treatment site comprises the steps of:
(a) positioning an ultrasound imaging device and the HIFU therapy device such that the focal point lies within an image plane provided by the ultrasound imaging device;
(b) providing an indication of where the focal point lies within an ultrasound image generated by the ultrasound imaging device, such that the focal point can be visualized in the ultrasound image, even when the HIFU therapy device is not energized;
(c) fixing a position of the ultrasound imaging device relative to the HIFU therapy device with a frame that couples the devices together, such that movement of either device will not move the focal point out of the image plane;
(d) obtaining the ultrasound image of the treatment site; and
(e) manipulating at least one of the ultrasound imaging device, the HIFU therapy device, and the frame until the indication of the focal point is properly positioned relative to the treatment site.

13. The method of claim 9, wherein the step of verifying that the focal point of the HIFU therapy device is properly positioned relative to the treatment site comprises the steps of:
(a) using an imaging device to obtain an image of the treatment site and adjacent areas;
(b) tracking a position of the imaging device;
(c) tracking a position of the HIFU therapy device;
(d) based on the positions of the imaging ultrasound transducer and the HIFU therapy device, introducing an icon into the image, the icon corresponding to a predicted position of the focal point based on the positions of the imaging device and the HIFU therapy device; and (e) manipulating the position of at least one of the imaging device and the HIFU therapy device until the icon coincides with the treatment site in the image.

14. A method for using ultrasound to simultaneously image a target area and to provide therapy to a treatment site disposed within said target area, the treatment site corresponding to a portion of a vascular system, where the therapy reduces an amount of blood flow into a mass of undesired tissue to indirectly damage the undesired tissue, comprising the steps of:

(a) positioning an imaging ultrasound transducer so as to enable an image of the target area to be obtained;

(b) positioning a therapeutic ultrasound transducer so that a focal point corresponding to the therapeutic ultrasound transducer generally coincides with a portion of the target area;

(c) energizing the imaging ultrasound transducer to generate an ultrasound image of the target area;

(d) selecting the treatment site from within the ultrasound image;

(e) energizing the therapeutic ultrasound transducer to produce pulses of high intensity focused ultrasound (HIFU) therapeutic waves to damage tissue at the treatment site, reducing the amount of blood flow into the mass of undesired tissue, so as to indirectly damage the undesired tissue by reducing a vascular supply of nutrients and oxygen to the undesired tissue; and (f) generating a plurality of ultrasound images during HIFU therapy, such that HIFU noise does not prevent the treatment site from being visualized in the plurality of ultrasound images, an interval between sequential ultrasound images being sufficiently small such that from a user's perspective, the sequence of ultrasound images provides real-time imaging during HIFU therapy.

15. The method of claim 14, further comprising a step of verifying a position of the focal point relative to the target area before energizing the therapeutic ultrasound transducer at a power level sufficient to reduce the amount of blood flow into the mass of undesired tissue, to reduce a risk that non-target structures will be damaged.

16. The method of claim 15, wherein the step of verifying a position of the focal point relative to the target area comprises the steps of:

(a) tracking a position of the imaging ultrasound transducer while producing the ultrasound image of the target area;

(b) tracking a position of the therapeutic ultrasound transducer;

(c) based on the positions of the imaging ultrasound transducer and the therapeutic ultrasound transducer, introducing an icon into the ultrasound image, the icon corresponding to a predicted position of the focal point based on the positions of the imaging ultrasound transducer and the therapeutic ultrasound transducer; and (d) manipulating a position of at least one of the imaging ultrasound transducer and the therapeutic ultrasound transducer until the icon coincides with the treatment site in the ultrasound image.

17. The method of claim 15, wherein the step of verifying a position of the focal point relative to the target area comprises the step of energizing the therapeutic ultrasound transducer at a power level that is insufficient to induce damage to tissue, but is sufficient to enable the focal point to be visualized in the ultrasound image, before energizing the therapeutic ultrasound transducer at a power level sufficient to achieve a desired therapeutic effect.

18. The method of claim 15, wherein the step of verifying a position of the focal point relative to the target area comprises the steps of:

(a) positioning the imaging ultrasound transducer and the therapeutic ultrasound transducer such that the focal point lies within an image plane provided by the imaging ultrasound transducer;

(b) providing an indication of where the focal point lies within the ultrasound image, such that the focal point can be visualized in the ultrasound image even when the therapeutic ultrasound transducer is not energized;

(c) fixing a position of the imaging ultrasound transducer relative to the therapeutic ultrasound transducer with a connecting frame, such that movement of either device will not move the focal point out of the ultrasound image; and (d) manipulating at least one of the imaging ultrasound transducer, the therapeutic ultrasound transducer, and the connecting frame until the indication of the focal point is positioned relative to the treatment site as desired.

* * * * *